(12) United States Patent
Matsumoto et al.

(10) Patent No.: US 9,568,488 B2
(45) Date of Patent: Feb. 14, 2017

(54) BIOLOGICAL SAMPLE ANALYZING APPARATUS

(75) Inventors: Teruya Matsumoto, Hyogo (JP); Yukie Nakazawa, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 1901 days.

(21) Appl. No.: 11/255,576

(22) Filed: Oct. 21, 2005

(65) Prior Publication Data

US 2006/0089810 A1 Apr. 27, 2006

(30) Foreign Application Priority Data

Oct. 22, 2004 (JP) .................................. 2004-308701

(51) Int. Cl.
| | |
|---|---|
| *G01N 33/48* | (2006.01) |
| *G01N 35/00* | (2006.01) |
| *G01N 15/02* | (2006.01) |
| *G01N 35/02* | (2006.01) |
| *G01N 15/00* | (2006.01) |
| *G01N 15/06* | (2006.01) |

(52) U.S. Cl.
CPC .... *G01N 35/00603* (2013.01); *G01N 15/0205* (2013.01); *G01N 35/028* (2013.01); *G01N 2015/0092* (2013.01); *G01N 2015/0693* (2013.01)

(58) Field of Classification Search
None
See application file for complete search history.

(56) References Cited

U.S. PATENT DOCUMENTS

| | | | |
|---|---|---|---|
| 4,472,505 A | | 9/1984 | Manabe et al. |
| 2003/0224534 A1* | | 12/2003 | Kawate .......................... 436/523 |
| 2005/0107956 A1 | | 5/2005 | Fukunaga et al. |

FOREIGN PATENT DOCUMENTS

| | | |
|---|---|---|
| JP | 56-150333 | 11/1981 |
| JP | S61-280568 A | 12/1986 |
| JP | 04-249744 | 9/1992 |
| JP | 05-099930 | 4/1993 |
| JP | 06-072845 B | 9/1994 |
| JP | 06-249856 | 9/1994 |
| JP | 08-247950 A | 9/1996 |
| JP | 2001-033451 A | 2/2001 |
| JP | 200133451 | * 2/2001 |

OTHER PUBLICATIONS

Simo et al., Clinical Chemistry, 1994, vol. 40, No. 4, p. 625-629.*
Morikawa et al., Clinical Biochemistry, 1995, vol. 28, No. 3, pp. 269-275.*
Surovtsev et al., Colloids and Surfaces B: Biointerfaces, Aug. 2003, vol. 32, Issue 3, p. 245-255.*
"Development of Dry-Type Immunoassay System and Reagents," *Japanese Journal of Clinical Laboratory Automation*, 1994, 19, No. 3, pp. 217-222 with partial translation.
Excerpt from Instruction Booklet for *ID-1000 Full Auto EIA Dry System* (*Toyobo*), 7 pages, with partial translation.

* cited by examiner

*Primary Examiner* — Pablo S Whaley
(74) *Attorney, Agent, or Firm* — Brinks Gilson & Lione

(57) ABSTRACT

In a biological sample analyzing apparatus and method, an assay sample is prepared by mixing a reagent with a biological sample which may contain assay material. Then, a first information relating to the assay material is collected from the assay sample, and when the first information satisfies predetermined condition, the assay material is analyzed based on the first information. However, when the first information does not satisfy the predetermined condition, a second information related to the assay material is collected from the assay sample, and the assay material is analyzed based on the second information.

10 Claims, 19 Drawing Sheets

T1

T2

US 9,568,488 B2

BIOLOGICAL SAMPLE ANALYZING APPARATUS

This application claims priority under 35 U.S.C. §119 to Japanese Patent Application No. 2004-308701 filed Oct. 22, 2004, the entire content of which is hereby incorporated by reference.

FIELD OF THE INVENTION

The present invention relates to an apparatus and method for analyzing assay material that contained in a biological sample.

BACKGROUND

Methods for quantifying assay material contained in a biological sample include methods in which material in an assay sample is agglutinated using a substance to induce an antigen-antibody reaction with the assay material, and the concentration of the assay material is calculated based on the degree of agglutination. Examples of such methods include immunoturbidity, immunonephelometry, counting immunoassay (CIA) and the like.

A calibration curve, which represents the relationship between the concentration of the assay material and information reflecting the degree of agglutination of the material in the assay sample, is used when calculating the concentration of the assay material by these methods. FIG. 14 shows an example of a calibration curve when the information reflecting the degree of agglutination of carrier particles is the absorbance in the immunoturbidity method using carrier particles. In FIG. 14, when the concentration of the assay material is in the low concentration range, the absorbance gradually increases in conjunction with the increase in the concentration of the assay material. However, above a certain concentration of the assay material (high concentration range), there is a reduction in the absorbency (referred to as a 'zone phenomenon'). As shown in FIG. 14, when the zone phenomenon occurs, two concentrations (C1 and C2) are obtained in the low concentration range and high concentration range of a single absorbency level A, such that the concentration of the assay material cannot be ultimately determined. Therefore, the concentration range in which the assay material can be measured is limited.

Japanese Laid-Open Patent Publication No. 61-280568 discloses a method for measuring an assay material even when the specimen contains a high concentration of assay material. This method utilizes CIA using carrier particles as the principle of measurement. CIA first mixes a specimen including an assay material and carrier particles on which antibody or antigen against the assay material is immobilized, and agglutinates the carrier particles by an antigen-antibody reaction. After a predetermined reaction time, the degree of agglutination is detected and the carrier particle distribution is obtained, then the degree of agglutination of the carrier particles is analyzed from the particle distribution, and the concentration of the assay material is calculated based on the degree of agglutination. The predetermined reaction time in this case is the time interval from the initiation of the antigen-antibody reaction until agglutination is detected.

In the method disclosed in Japanese Laid-Open Patent Publication 61-280568, a calibration curve is prepared across the entire region including the low concentration range and high concentration range, and the agglutination of the carrier particles is determined for the reaction time T1 and reaction time T2 of the antigen-antibody reaction. Then, a concentration is calculated from the degree of agglutination and calibration curve at reaction time T1, and another concentration is calculated from the degree of agglutination and calibration curve at reaction time T2. In this way the concentrations are compared for the reaction time T1 and reaction time T2, and a concentration common to both reaction time T1 and reaction time T2 is designated as the final assay material concentration.

The method of Japanese Laid-Open Patent Publication No. 61-280568 is described below using FIG. 15. FIG. 15 shows the calibration curves at reaction time T1 and reaction time T2 (where T1<T2). In FIG. 15, calibration curve T1 is the calibration curve at reaction time T1, and calibration curve T2 is the calibration curve at reaction time T2. For example, when the agglutination at reaction time T2 is designated B, the concentration of the assay material is either C1 or C2. Likewise, when the agglutination at reaction time T1 is A1, the concentration C1, which is common to each reaction time on the calibration curves, becomes the concentration of the assay material in the specimen. Similarly, when the agglutination at reaction time T1 is A2, the concentration C2, which is common to each reaction time on the calibration curves, becomes the concentration of the assay material in the specimen.

However, the value of the degree of agglutination at reaction time T2 is indispensable for determining the concentration of the assay material in this method. That is, the degree of agglutination at both reaction times T1 and T2 are invariably required in this method.

BRIEF SUMMARY

The scope of the present invention is defined solely by the appended claims, and is not affected to any degree by the statements within this summary. The present invention provides a biological sample analyzing apparatus and biological sample analyzing method providing improved efficiency in biological sample analysis over the conventional art.

A first aspect of the present invention relates to a biological sample analyzing apparatus comprising: an assay sample preparing mechanism for preparing assay sample by mixing testing reagent and a biological sample; a measuring unit for collecting information relating to an assay material contained in the biological sample from the assay sample; a first control means for controlling the measuring unit such that the measuring unit collects a first information relating to the assay material; a first analyzing means for analyzing the assay material based on the first information when the first information satisfies a predetermined condition; a second control means for controlling the measuring unit such that the measuring unit collects a second information relating to the assay material when the first information does not satisfy the predetermined condition; and a second analyzing means for analyzing the assay material based on the second information.

A second aspect of the present invention relates to a biological sample analyzing apparatus comprising: an assay sample preparing mechanism for preparing assay sample by mixing testing reagent and a biological sample; a measuring unit for detecting transmitted light from an assay sample, and collecting information of change in absorbance based on the detected transmitted light; a first control means for controlling the measuring unit so as to collect a first information of change in absorbance based on the transmitted light detected at a first time and a second time, wherein the first time and the second time are times after the assay sample preparing mechanism has prepared the assay sample; a first analyzing means for analyzing an assay material contained in the biological sample based on the first information when the first information satisfies a predetermined condition; a second control means for controlling the measuring unit so as to collect a second information of change in absorbance based on the transmitted light detected at a third time and a fourth time when the first information does not satisfy the predetermined condition, wherein the third time and the fourth time are times after the assay sample preparing mechanism has prepared the assay sample; and a second analyzing means for analyzing the assay material based on the second information.

A third aspect of the present invention relates to a biological sample analyzing method comprising the steps of: (a) preparing an assay sample by mixing testing reagents and a biological sample; (b) collecting a first information relating to an assay material contained in the biological sample from the assay sample; (c) analyzing the assay material based on the first information when the first information satisfies a predetermined condition; (d) collecting a second information relating to the assay material from the assay sample when the first information does not satisfy the predetermined condition; and (e) analyzing the assay material based on the second information.

DETAILED DESCRIPTION OF THE DRAWINGS AND THE PRESENTLY PREFERRED EMBODIMENTS

Figure 1:
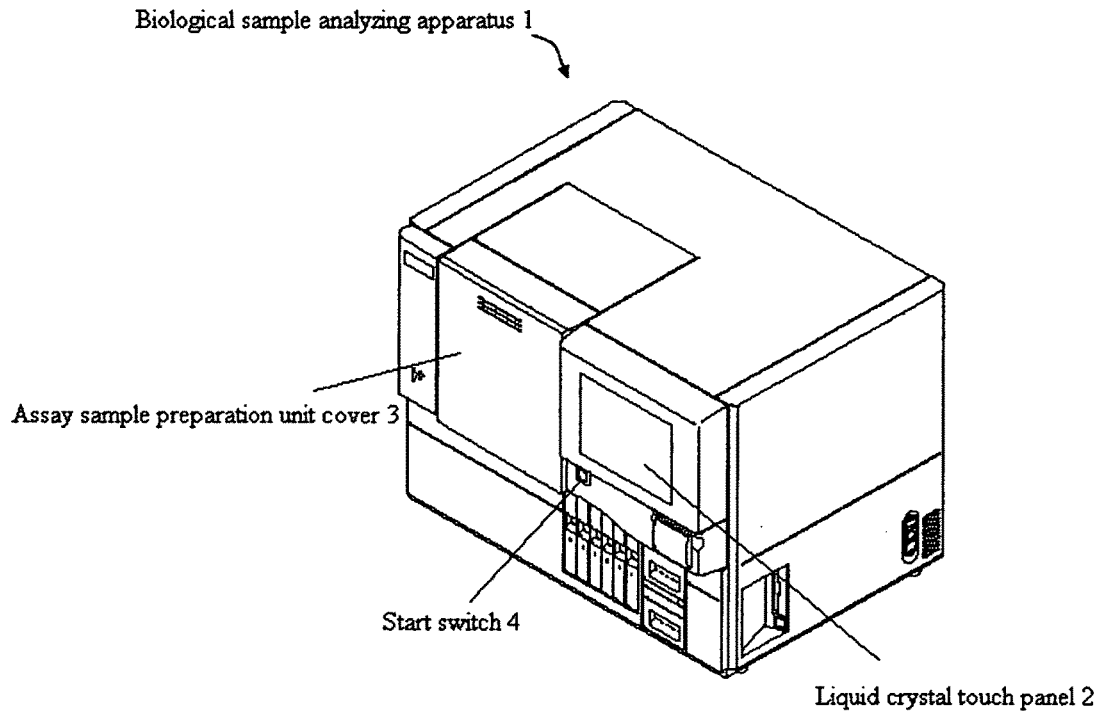
FIG. 1 shows an external view of an embodiment of the biological sample analyzing apparatus of the present invention.

In a biological sample analyzing apparatus and method of an embodiment, first an assay sample is prepared by mixing a reagent with a biological sample which may contain assay material. Then, a first information relating to the assay material is collected from the assay sample, and when the first information satisfies predetermined condition, the assay material is analyzed based on the first information. However, when the first information does not satisfy the predetermined condition, a second information related to the assay material is collected from the assay sample, and the assay material is analyzed based on the second information. Therefore, the first information and the second information need not be collected for all biological samples, and the second information is collected only when the first information does not satisfy predetermined condition. In this way, it is possible to improve efficiency when analyzing biological samples.

The method of analyzing biological samples comprises a method in which an assay material contained in a biological sample, such as blood and the like, is measured using an antigen-antibody reaction. Biological sample analyzing methods in which an assay material is measured using an antigen-antibody reaction include, for example, immunoturbidity methods, immunonephelometry, counting immunoassay (CIA) and the like.

The biological samples used as the biological samples in the aforesaid analyzing method are not specifically limited, and may be, for example, urine, and blood samples such as whole blood, plasma, and serum and the like.

The assay materials that are analyzable by the aforesaid analyzing method are not specifically limited, and may be, for example, immunoglobulin (IgG, IgA, IgM, IgD, IgE), complements (C3, C4, C5, C1q), C-reactive protein (CRP), α-fetoprotein (AFP), β2-microglobulin, carcinoembryonic antigen (CEA), prostate specific antigen (PSA), anti HCV antibody, insulin, ferritin and the like.

The reagents used in the aforesaid analysis method are not specifically limited, and may be, for example, reagents containing substances that induce an antigen-antibody reaction with the assay material. Substances that induce an antigen-antibody reaction with the assay material may be an antigen that produces a specific antigen-antibody reaction with the antibody when the assay material is an antibody, and may be an antibody that produces a specific antigen-antibody reaction with the antigen when the assay material is an antigen. For example, an anti CRO antibody may be used in the case of an assay material that is a CRP antigen marker for infection and myocardial infarction.

Furthermore, Immunoturbidity method that use carrier particles, immunonephelometry method that use carrier particles, and counting immunoassay method use carrier particles on which the substance that produces an antibody-antigen reaction with the assay material are immobilized. For example, when the assay material is a CRP antigen, carrier particles on which anti CRP antibody is immobilized may be used. The carrier particles typically used in the aforesaid analyzing method includes, for example, latex particles, magnetic particles, metal particles, dendrimer and the like.

The information relating to the assay material comprises information which generally used in methods that measure an assay material contained in a biological sample using an antigen-antibody reaction. For example, transmitted light and absorbance in the immunoturbidity methods and scattered light in the immunonephelometry methods may be used as the information relating to the assay material. Furthermore, the change in transmitted light, absorbance or scattered light per a predetermined time may be used. The rate of agglutination of carrier particles in the CIA method may also be used. The rate of agglutination in the CIA method can be determined based on information that reflects the size of particles (hereinafter referred to as 'size information'). When unagglutinated carrier particles (hereinafter referred to as 'independent particles') and clusters formed by a plurality of agglutinated carrier particles (hereinafter referred to as 'aggregates') are compared, the apparent size of the aggregate is larger. Therefore, independent particles and aggregates can be differentiated and counted separately and the rate of agglutination of carrier particles can be determined by detecting the size information. For example, the value of P/T can be used as the agglutination rate. The value of P/T is calculated based on the total number of particles (T) obtained by adding the number of independent particles (M) and the number of aggregates (P). The optical information of the scattered light can be used as the size information. Furthermore, electrical information representing the direct current resistance obtained when the particles cross between electrodes through which a direct current flow may be used as an alternative to optical information.

In the method for analyzing biological samples, a first information related to an assay material is collected from an assay sample, and the assay material is analyzed based on the first information when the first information satisfies predetermined condition. However, when the first information does not satisfy the predetermined condition, a second information related to the assay material is collected from the assay sample, and the assay material is analyzed based on the second information. The predetermined condition is used to determine whether or not the assay material can be measured using the first information. For example, when a threshold value X is provided for the first information and a condition is set such that "the assay material is measured based on the first information when the first information is equal to or greater than X." Then the assay material is measured based on the first information when the first information obtained by a measurement is equal to or greater than X, and the assay material is measured based on a second information when the first information is less than X. This condition may be suitably set in accordance with the type of measurement method and type of assay material while considering the reliability of the result obtained by the measurement based on the first information.

The biological sample analyzing apparatus 1 of one embodiment of the present invention is described hereinafter. The biological sample analyzing apparatus 1 uses the measurement principles of the CIA method.

The biological sample analyzing apparatus 1 prepares an assay sample by mixing a carrier particle suspension and reaction buffer solution with a specimen, such as blood, urine or the like. Carrier particles suspended in a suitable fluid, such as water, buffer solution or the like, may be used as the particle suspension. If an assay material is present in the specimen, the carrier particles agglutinate by an antigen-antibody reaction when the carrier particle suspension is added to the specimen. The reaction buffer solution may be added to the carrier particle suspension and specimen to adjust the environment in which the antigen-antibody reaction is produced. The biological sample analyzing apparatus 1 illuminates the prepared assay sample with laser light, detects optical information emitted from the assay sample, and calculates the carrier particle agglutination rate based on the detected optical information. The optical information is detected at a predetermined reaction time. The predetermined reaction time in this case is the time interval from the initiation of the antigen-antibody reaction until agglutination is detected. The biological sample analyzing apparatus 1 calculates the carrier particle agglutination rate based on the optical information detected at reaction time T1. Then, the value of the agglutination rate at reaction time T1 is compared to a predetermined threshold value, and a determination is made as to whether or not measurement at reaction time T2 (T1<T2) is required. When the value of the agglutination rate at reaction time T1 is equal to or greater than the predetermined threshold value, the assay material is measured based on a calibration curve and the agglutination rate at reaction time T1 without performing a measurement at reaction time T2. However, when the value of the agglutination rate at reaction time T1 is less than the predetermined threshold value, a measurement is performed at reaction time T2 to obtain a measurement result of higher reliability since the measurement result at reaction time T1 has a low reliability. In this case, the optical information at reaction time T2 is detected, and the agglutination rate at reaction time T2 is calculated based on the detected optical information. Then, the assay material contained in the specimen is measured based on a calibration curve and the agglutination rate at reaction time T2. The calibration curves represent the relationship between the agglutination rate and the assay material, and are prepared by measuring a standard solution consisting of a fluid containing a known concentration of the assay material. When preparing a calibration curve, a plurality of standard solutions are used which have graduatedly different concentrations of included assay material. In the biological sample analyzing apparatus 1, forward scattered light is used as the optical information.

(General Structure of Biological Sample Analyzing Apparatus 1)

Figure 2:
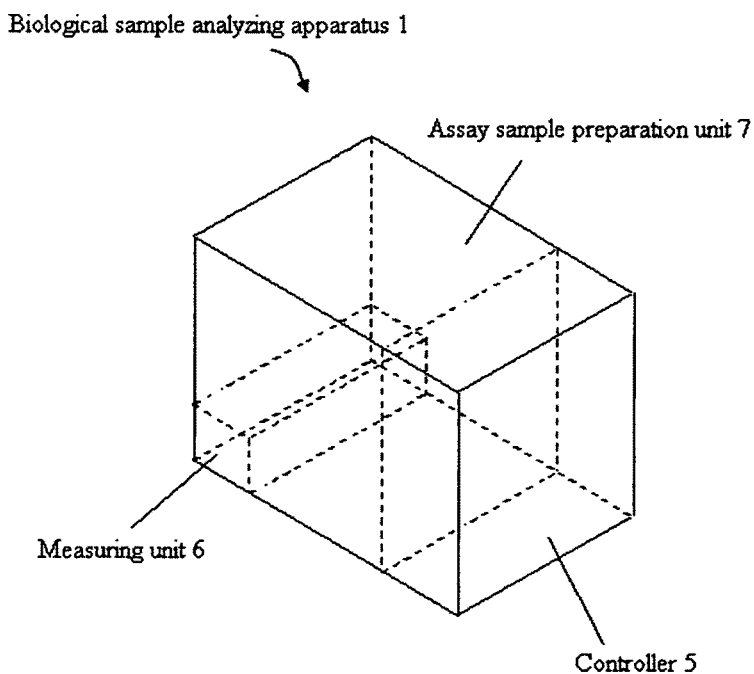
FIG. 2 shows the internal structure of the embodiment of the biological sample analyzing apparatus of the present invention.

FIG. 1 is an external view of the biological sample analyzing apparatus 1. A liquid crystal touch panel 2 for inputting various settings and displaying measurement results, assay sample preparation unit cover 3, and start switch 4 are arranged on the front of the apparatus 1. FIG. 2 shows the internal structure of the biological sample analyzing apparatus 1. A controller 5 for controlling the operation and analyzing process of the apparatus is arranged in a space at the right side of the apparatus 1. A measuring unit 6 for detecting signals from the assay sample is arranged in a space on the lower left side of the apparatus 1. An assay sample preparation unit 7 for preparing the assay sample is arranged in the remaining space.

(Structure of the Assay Sample Preparation Unit)

Figure 3:
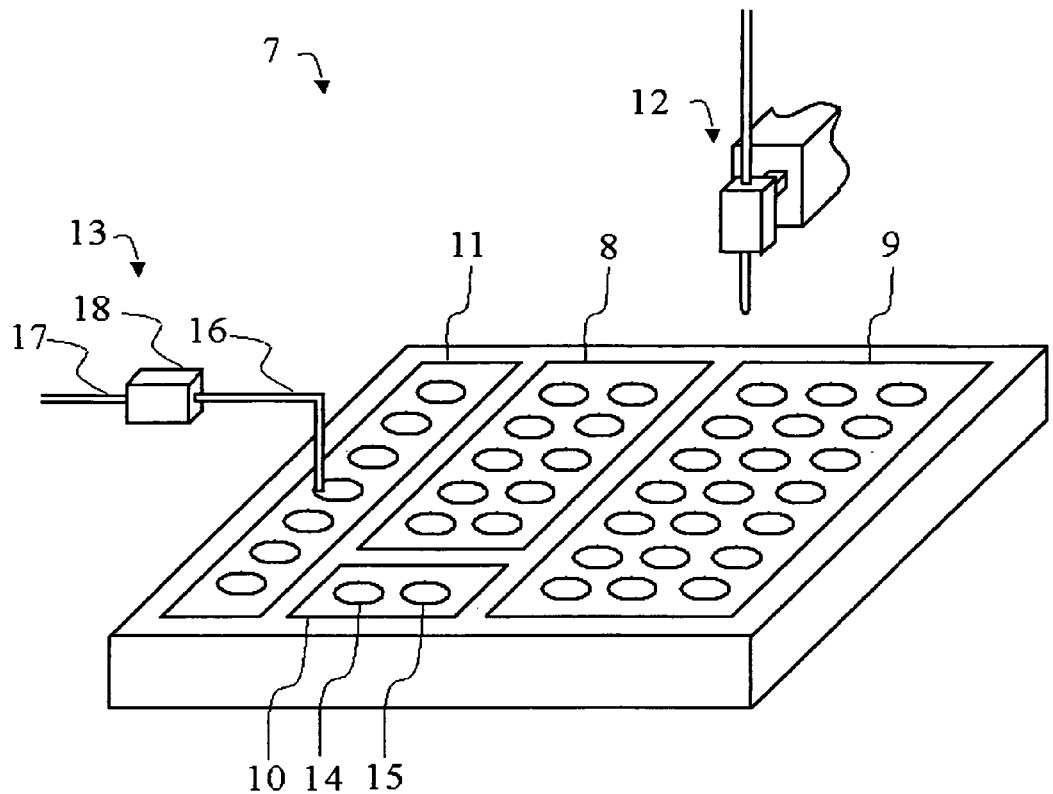
FIG. 3 shows the assay sample preparation unit of the embodiment of the biological sample analyzing apparatus of the present invention.

FIG. 3 shows the assay sample preparation unit 7. The assay sample preparation unit 7 includes a specimen placement unit 8, standard solution placement unit 9, reagent placement unit 10, reaction unit 11, dispensing unit 12, and fluid delivery device 13. An operator places a container containing a specimen in the specimen placement unit 8 by opening the assay sample preparation unit cover 3. The operator places a container containing standard solution in the standard solution placement unit 9. The operator respectively places a container 14 containing reaction buffer solution and a container 15 containing carrier particle suspension in the reagent placement unit 10. A container is placed in the reaction unit 11, an assay sample is prepared by mixing the reaction buffer solution and carrier particle suspension with the specimen or standard solution in the container. Although not shown in the drawing, the reaction unit 11 is provided with a mixing device for mixing the fluids in the container, and a temperature regulating device for maintaining the fluid in the container at a constant temperature. The tip of the dispensing unit 12 suctions and discharges a predetermined amount of fluids, and is also movable in vertical and front-to-back directions by means of a drive device not shown in the drawing. The fluid delivery device 13 includes a suction tube 16 for suctioning the assay sample, delivery tube 17 for delivering assay sample suctioned from the suction tube 16 to the measuring unit 6 shown in FIG. 4, and a pump 18 for suctioning and delivering the assay sample to the measuring unit 6. Furthermore, the fluid delivery device 13 is movable in vertical and front-to-back directions by a drive device not shown in the drawing, so as t insert the suction tube 16 in the container placed in the reaction unit 11 and suction a predetermined amount of assay sample. The suctioned assay sample is delivered through the fluid delivery system 17 to the measuring unit 6.

(Structure of the Measuring Unit)

Figure 4:
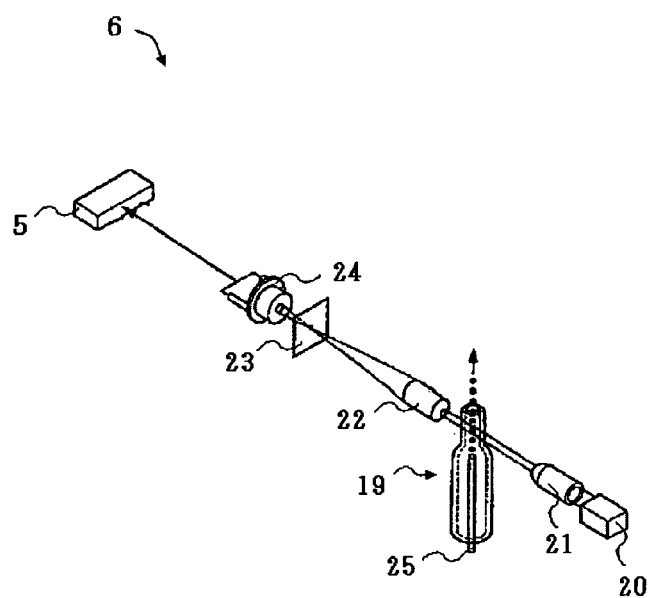
FIG. 4 shows the measurement unit of the embodiment of the biological sample analyzing apparatus of the present invention.
Figure 5:
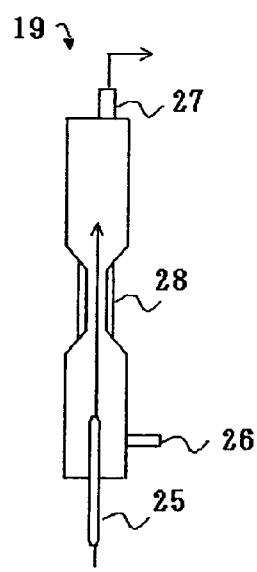
FIG. 5 shows the sheath flow cell of the embodiment of the biological sample unit of the present invention.

FIG. 4 shows the measuring unit 6. The measuring unit 6 is provided with a sheath flow cell 19, laser light source 20, condenser lens 21, collective lens 22, pinhole 23, and photodiode 24. The sheath flow cell 19 is provided for the flow of the assay sample prepared by the previously described assay sample preparation unit 7 shown in FIG. 3. As shown in FIG. 5, the sheath flow cell 19 is provided with a sample nozzle 25 for spraying assay sample upward toward a fine bore part 28, a sheath fluid inlet 26, and waste fluid outlet 27. The collective lens 22 collects the forward scattered light obtained from each individual particle in the sample illuminated by laser light. The photodiode 24 receives the forward scattered light, subjects the light to photoelectric conversion, and outputs the resulting electrical signal. Each output signal is transmitted to the controller 5.

(Structure of the Controller)

Figure 6:
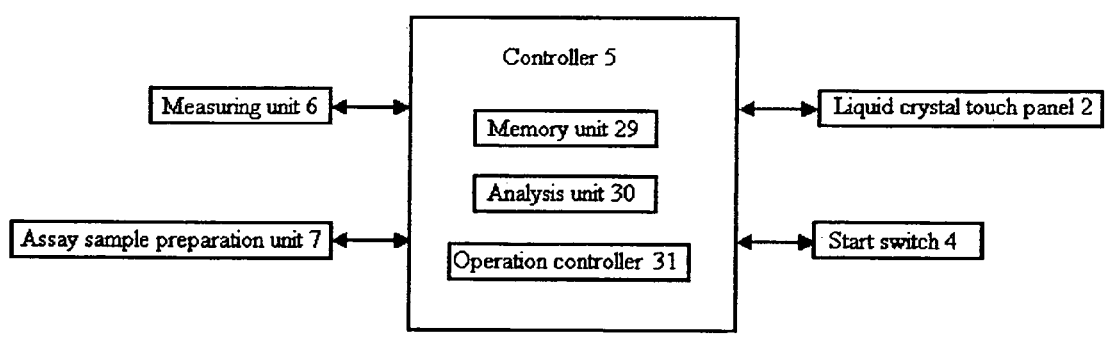
FIG. 6 shows the relationship between each part of the apparatus and the controller of the embodiment of the biological sample analyzing apparatus of the present invention.

FIG. 6 is a block diagram showing the structure of the controller 5, and the relationship between the controller 5 and each unit. The controller 5 has a microcomputer provided with a central processing unit (CPU), and memory devices such as ROM, RAM and the like, and circuits for processing the signals received from the measuring unit 6. The controller 5 functions as the analyzing unit 30, and operation controller 31. The memory unit 29 stores an analysis program for analyzing the signals obtained from the particles in the sample, and a control program for controlling the operation of each part of the apparatus. The memory unit 29 also stores the data of the signals detected by the measuring unit 6, and the processing results of the analysis program. The analyzing unit 30 analyzes the signals detected by the measuring unit 6 based on the analysis program, and generates data related to each particle contained in the assay sample. The data generated by the analyzing unit 30 are output to the liquid crystal touch panel 2. The operation controller 31 controls the operation of each part of the apparatus based on the control program stored in the memory unit 29.

The operation of the biological sample analyzing apparatus 1 is described in detail below. An operator first places the standard solution, specimen, and reagents at the predetermined positions in the assay sample preparation unit 7. A standard solution is used at reaction time T1 and a standard solution is used at reaction time T2; each standard solution consists of a plurality of standard solutions having graduatedly different concentrations of included assay material. The respective standard solutions can be placed in the standard solution placement unit 9 of the assay sample preparation unit 7 shown in FIG. 3 by opening the assay sample preparation unit cover 3 shown in FIG. 1. The specimen can be placed in the specimen placement unit 8 of the assay sample preparation unit 7. Furthermore, the container 14 containing reaction buffer and the container 15 containing carrier particle suspension can be respectively placed in the reagent placement unit 10 of the assay sample preparation unit 7.

Figure 7:
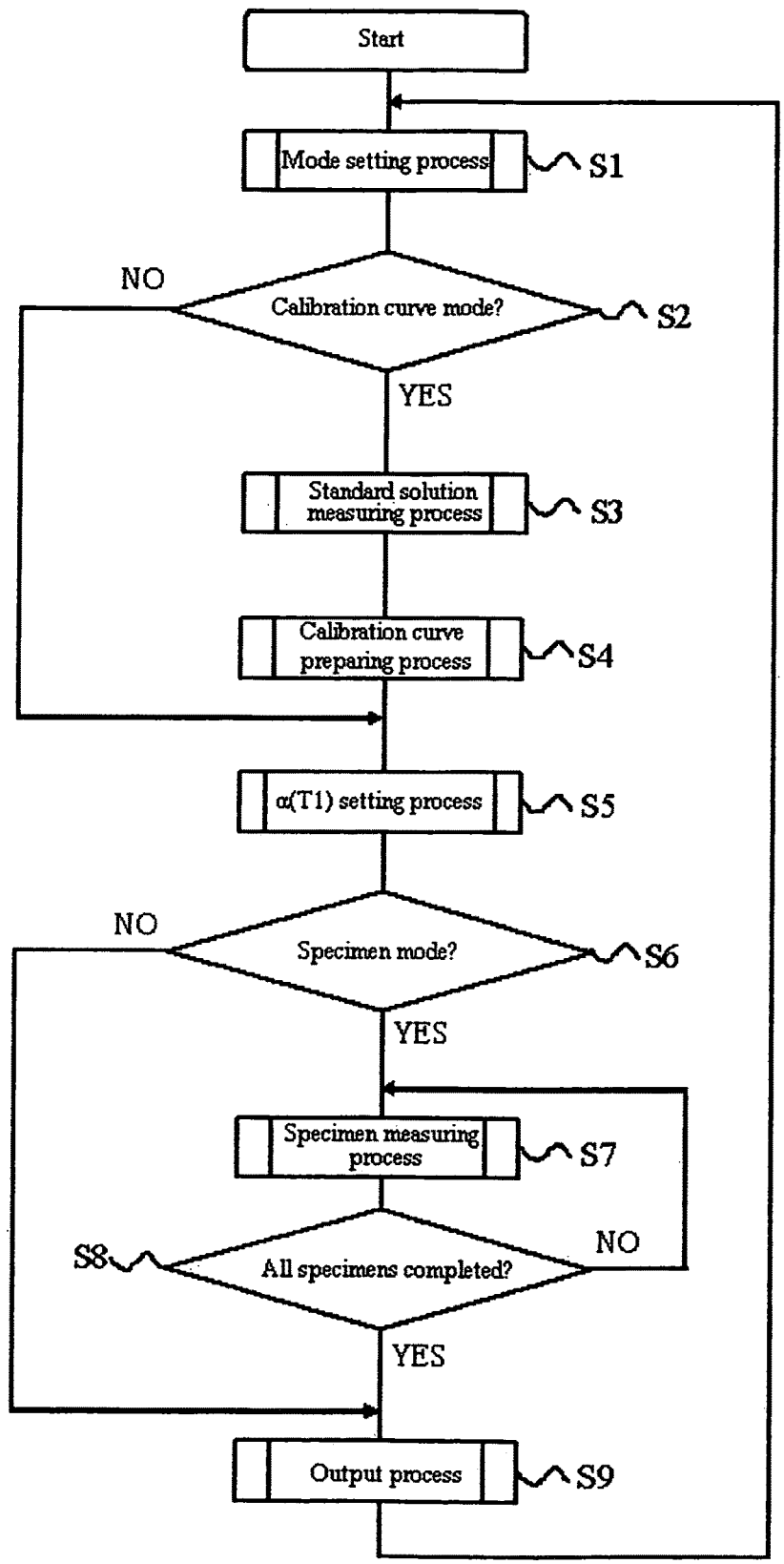
FIG. 7 illustrates the flow of the overall control of the embodiment of the biological sample analyzing apparatus of the present invention.

FIG. 7 is a flow chart showing the general control flow of the control program. In step S1 (mode setting process), a condition setting screen is displayed on the liquid crystal touch screen 2. In the biological sample analyzing apparatus 1, there are two measurement modes, which include the a calibration curve mode for measuring the standard solutions and preparing calibration curves, and a specimen mode for measuring a specimen and quantifying the assay material contained in the specimen; each mode is selectable by the operator in accordance with the measurement to be performed. The operator enters various settings in the displayed condition setting screen, for example, the measurement mode, reaction time which is time from the start of the antigen-antibody reaction by the addition of the carrier particle suspension until agglutination is detected, concentrations of the assay material contained in each standard solution and the like. When setting input of step S1 ends, step S2 (discrimination of the calibration curve mode selection), step S3 (standard solution measuring process), step S4 (calibration curve preparation process), step S5 ($\alpha$(T1) setting process), step S6 (discrimination of the specimen mode selection), step S7 (specimen measuring process), step S8 (all specimens completion), and step S9 (output process) are sequentially executed.

For example, when only calibration curve preparation is performed, only the calibration mode is selected in the mode setting process of step S1. In this case, in the subsequent step S2, 'calibration mode is set' is discriminated, and then in step S3 the measurement of each standard solution is sequentially performed. When the measurement of all standard solutions is completed in step S3, the process continues to step S4 and calibration curves are respectively prepared at reaction times T1 and T2. (Hereinafter, the calibration curve at reaction time T1 is referred to as calibration curve T1, and the calibration curve at reaction time T2 is referred to as calibration curve T2.) When the calibration curves have been prepared in step S4, the process continues to step S5. In step S5, the threshold value of the agglutination rate at reaction time T1 is set at $\alpha$(T1). In the biological sample analyzing apparatus 1, the value of the agglutination rate at reaction time T1 is compared with the predetermined threshold value, and a determination is made as to whether or not to perform a measurement at reaction time T2 (T1<T2). The value $\alpha$(T1) set in step S5 is equivalent to the predetermined threshold value. When $\alpha$(T1) is set in step S5, the process advances to step S6. In step S6, "specimen mode not set" is determined, and the process advances to step S9 and the data, such as the standard solution agglutination rate and calibration curves and the like, are output.

When the calibration curves have already been prepared and only specimen measurements are to be performed, only the specimen mode is selected in the mode setting process of step S1. In this case, in the subsequent step S2, 'calibration mode is not set' is discriminated, and then $\alpha$(T1) is set in step S5. When $\alpha$(T1) is set in step S5, the process advances to step S6. In step S6, "specimen mode is set" is determined, and the process advances to step S7 and the specimen is measured. When measuring a plurality of specimens, "measurement of all specimens not completed" is determined in step S8, and step S7 is repeated. When the measurement of all specimens has been completed, the process advances to step S9 and the data, such as the specimen measurement results and the like, are output.

When both calibration curve preparation and specimen measurement are performed, both the calibration curve mode and specimen mode are selected in the mode setting process of step S1. In this case, the calibration curves are prepared through steps S1, S2, S3, and S4, and thereafter $\alpha$(T1) is set in step S5. When $\alpha$(T1) is set in step S5, the process advances to step S6. In step S6, "specimen mode is set" is determined, and the process advances to step S7 and the specimens are measured through step S8. When the measurement of all specimens has been completed, the process advances to step S9 and the data, such as the calibration curves and specimen measurement results and the like, are output. The assay sample preparation unit 7, measuring unit 6, and analyzing unit 29 are controlled by the control program, and their sequential operations are automatically performed from steps S1 through S9. Each step is described below.

S1 (Mode Setting Process)

Figure 8A:
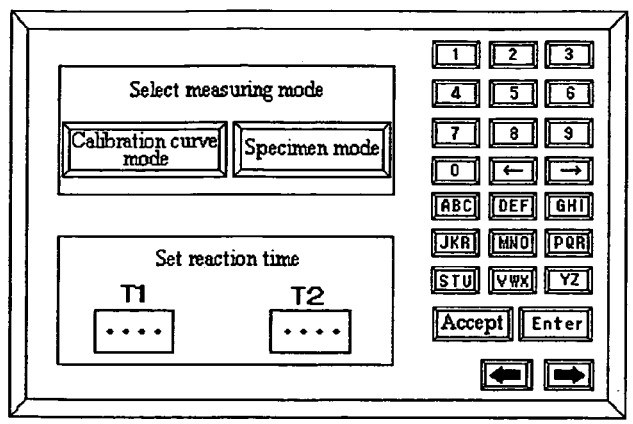
FIG. 8A shows an example of a measurement setting screen displayed on a liquid crystal touch panel of the embodiment of the biological sample analyzing apparatus of the present invention.
Figure 8B:
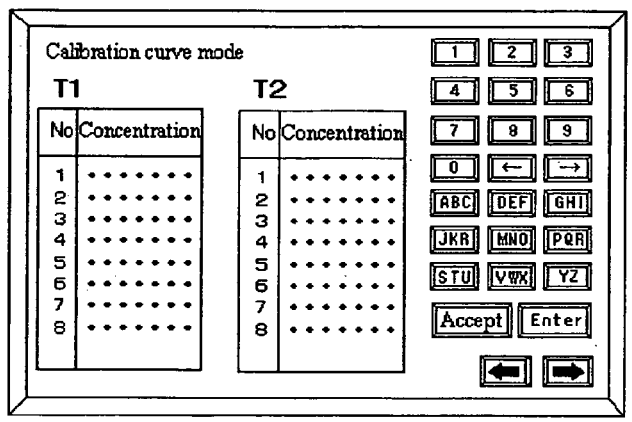
FIG. 8B shows an example of a measurement setting screen displayed on a liquid crystal touch panel of the embodiment of the biological sample analyzing apparatus of the present invention.
Figure 8C:
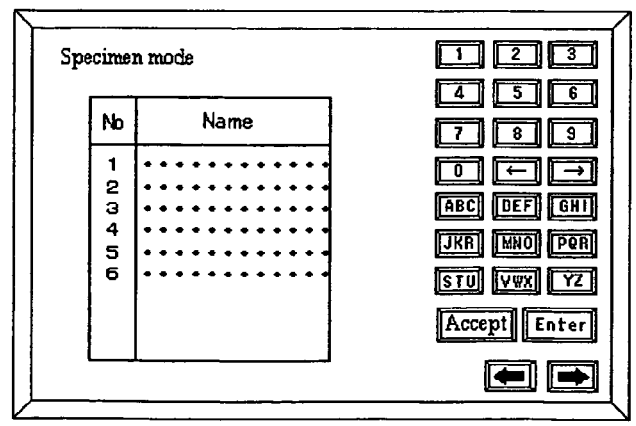
FIG. 8C shows an example of a measurement setting screen displayed on a liquid crystal touch panel of the embodiment of the biological sample analyzing apparatus of the present invention.
Figure 9:
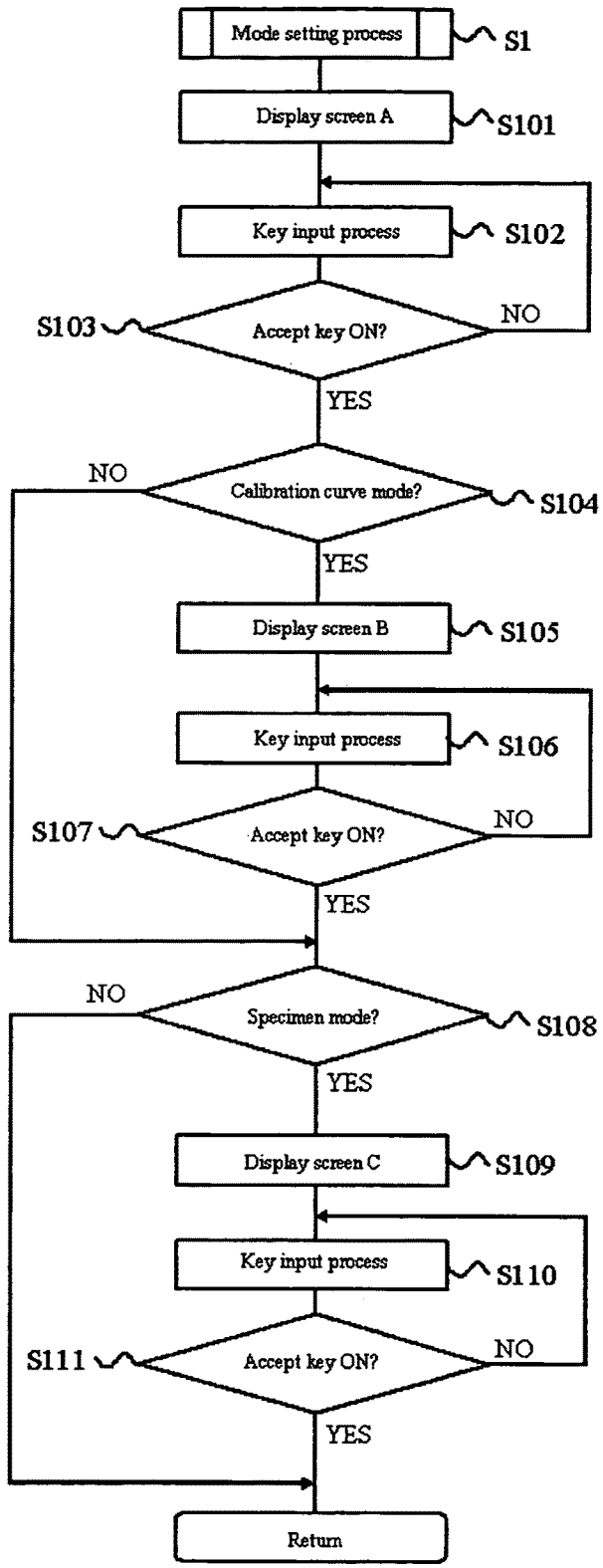
FIG. 9 illustrates the flow of the mode setting process in the embodiment of the present invention.

The mode setting process is described below referring to FIGS. 8 and 9. FIG. 8 shows the screens displayed on the liquid crystal touch panel 2 during the mode setting process. Various types keys are displayed on the screens, and a key is selected when the operator uses a finger or the like to touch a position at which a key is displayed on the liquid crystal touch panel 2. FIG. 9 is a flow chart showing the flow of the mode setting process. Each step of the flow chart is described below.

S101: The screen A shown in FIG. 8A is displayed on the liquid crystal touch panel 2. Then, the process advances to step S102.

S102: the measurement mode and reaction time settings are entered on the screen A. A key for operator selection of the measurement mode is provided at the upper left side of the screen A. Calibration curves are prepared when the [calibration mode] key is selected, and a specimen is measured when the [specimen mode] key is selected. Furthermore, when both the [calibration mode] key and the [specimen mode] key are selected, the specimen is measured after the calibration curves have been prepared. Boxes for the operator to enter the reaction times T1 and T2 are provided in the lower left of the screen A. A ten-key pad is provided on the right side of the screen A for entering numerical values in each box. When setting input on screen A has been completed, the process moves to step S103.

S103: An [Accept] key is displayed on the screen A, and the selection of the [Accept] key by the operator is received in step S103. When the [Accept] key has been selected, the process continues to step S104.

S104: When [calibration mode] is selected in step S102, the process continues to step S105. However, when [calibration mode] is not selected in step S102, the process advances to step S108.

S105: The screen B shown in FIG. 8B is displayed on the liquid crystal touch panel 2. Then, the process continues to step S106.

S106: The setting inputs related to the calibration curve, such as the number and concentrations of each standard solution used to prepare the calibration curves, are received on the screen B. Boxes for the operator to enter the number and concentrations of each standard solution are provided on the left side of the screen B. A ten-key pad is provided on the right side of the screen B for entering numerical values in each box. When setting input on screen B has been completed, the process moves to step S107.

S107: The [Accept] key is displayed on the screen B, and the operator selection of the [Accept] key is received in step S107. When the [Accept] key has been selected, the process continues to step S108.

S108: When the [specimen mode] is selected in step S102, the process continues to step S109. When the [specimen mode] has not been selected in step S102, however, the mode setting process ends.

S109: The screen C shown in FIG. 8C is displayed on the liquid crystal touch panel 2. Then, the process advances to step S110.

S110: Setting inputs related to the specimen mode, such as specimen number and specimen name and the like, are received on screen C. Boxes for the operator to enter the number and name of each specimen are provided on the left side of the screen C. A ten-key pad is provided on the right side of the screen C for entering numerical values and text in each box. When setting input on screen C has been completed, the process moves to step S111.

S111: The [Accept] key is displayed on the screen C, and the operator selection of the [Accept] key is received in step S111. When the [Accept] key has been selected, the mode setting process ends.

S2 (Calibration Mode Selection Determination)

In step S2, a determination is made as to whether or not the calibration mode has been selected based on the measurement conditions input in the mode setting process of step S1. When [calibration mode] has been selected in step S1, the process continues to step S3 (standard solution measuring process). When [calibration mode] is not selected in step S1, however, the process advances to step S5 ($\alpha$(T1) setting process).

S3 (Standard Solution Measuring Process)

Figure 10:
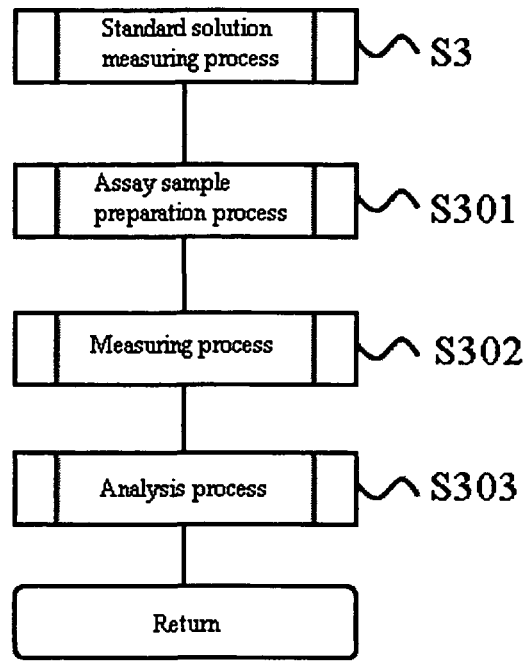
FIG. 10 illustrates the flow of the standard fluid measuring process in the embodiment of the present invention.

In step S3, the standard solutions containing known concentrations of assay material are measured. FIG. 10 is a flow chart showing the flow of the standard solution measuring process. In the standard solution measuring process, step S301 (assay sample preparation process), step S302 (measuring process), and step S303 (analysis process) are sequentially performed. Steps S301, S302, and S303 are described below.

S301 (Assay Sample Preparation Process)

The operation of the assay sample preparation unit 7 in step S301 is described referring to FIG. 3. First, the dispensing unit 12 suctions standard solution from the container placed in the standard solution placement unit 9, and dispenses 10 µL to the container placed in the reaction unit 11. Then, the dispensing unit 12 suctions reaction buffer from the container 14 placed in the reagent placement unit 10, and dispenses 80 µL to the container placed in the reaction unit 11. Then, the dispensing unit 12 suctions carrier suspension from the container 15 placed in the reagent placement unit 10, and dispenses 10 µL to the container placed in the reaction unit 11. The antigen-antibody reaction is started by the addition of the carrier particle suspension. The assay sample in the container in the reaction unit 11 is agitated while maintained at a temperature of 45° C. Then, the fluid delivery device 13 suctions 14.5 µL of the assay sample in the container in the reaction unit 11, and delivers the sample to the sheath flow cell 19 of the measuring unit 6.

When preparing a calibration curve, a plurality of standard solutions are used which have graduatedly different concentrations of included assay material. Therefore, a plurality of T1 standard solutions are placed in the standard solution placement unit 9. Then, assay samples are sequentially prepared from the standard solutions of each concentration placed in the standard solution placement unit 9. Thus, when assay samples are prepared from the standard solutions, the subsequent steps S302 and S303 described later are sequentially executed. Then the agglutination rate at reaction time T1 is calculated for the assay samples prepared from the T1 standard solutions, and the agglutination rate at reaction time T2 is calculated for the assay samples prepared from the T2 standard solutions.

S302 (Measuring Process)

The operation of the measuring unit 6 in the measuring process is described below referring to FIGS. 4 and 5. In the measuring process, after the carrier particle suspension has been added and the antigen-antibody reaction has started, 14.5 µL of the assay sample is suctioned from the container in the reaction unit 11 by the fluid delivery device 13 and delivered to the sheath flow cell 19 of the measuring unit 6. The assay sample delivered to the sheath flow cell 19 is discharged from the sample nozzle 25 into the sheath flow cell. Sheath fluid is also discharged from the sheath fluid inlet 26 into the sheath flow cell at the same time as the aforesaid operation. In this way the sample fluid is encapsulated in sheath fluid within the sheath flow cell, and then the flow is narrowly constricted by the fine bore part 28. The sample fluid flows in the fine bore part 28 and the particles contained in the sample fluid can be adjusted to form a line by the constricting the flow to the same degree as the particle diameter.

Laser light emitted from the laser light source 20 is constricted by the condenser lens 21, and irradiates the sample flowing through the fine bore part 28. The forward scattered light from each individual particle in the sample illuminated by the laser light is collected by the collective lens 22 and passes through the pinhole 23. The forward scatter light that passes through the pinhole 23 is received by the photodiode 24, subjected to photoelectric conversion, and output as a forward scattered light signal. Each output signal is transmitted to the controller 5, and stored in the memory unit 29 as data for each particle. Thus, the forward scattered light from the assay sample is detected at predetermined reaction times in step S302. These predetermined reaction times are the reaction time T1 and reaction time T2 set in step S1.

S303 (Analysis Process)

Figure 11:
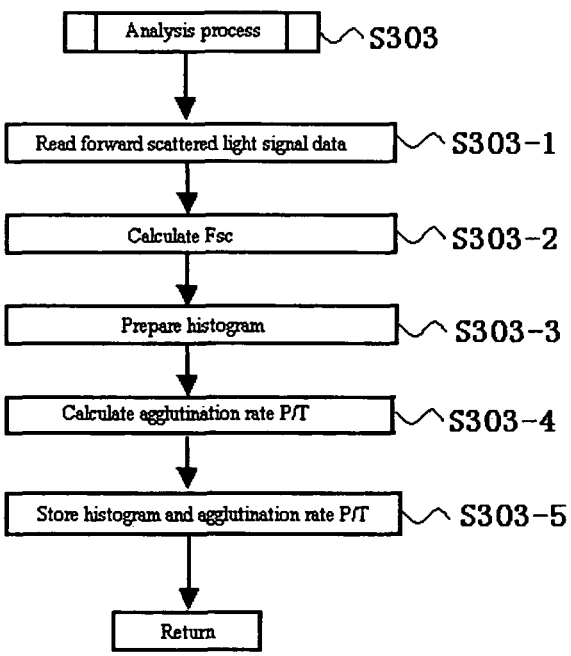
FIG. 11 illustrates the flow of the analysis process in the standard fluid measuring process in the embodiment of the present invention.

When the forward scattered light is detected in step S302, analysis is executed by the analyzing unit 30 based on the analysis program. The operation of the analysis program in step S303 is described below using the flow chart of FIG. 11. Each step of the flow chart is described below.

Step S303-1: The data of the forward scattered light signals are read from the memory unit 29. Then, the process moves to step S303-2.

S303-2: The forward scatter light intensity (Fsc) is calculated for each particle in the sample fluid based on the data of the forward scattered light signals. Then, the process continues to step S303-3.

Figure 16:
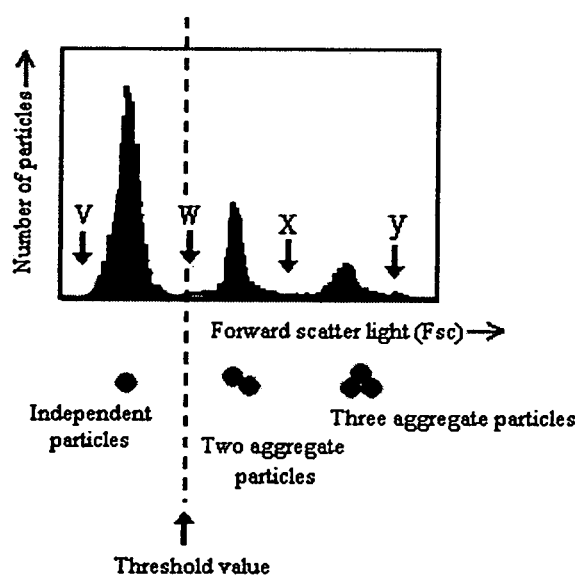
FIG. 16 shows an example of a histogram.

S303-3: A carrier particle histogram is prepared. FIG. 16 shows an example of a histogram prepared based on the carrier particle Fsc; the number of particles are plotted on the vertical axis, and the Fsc is plotted on the horizontal axis. Then, the process continues to step S303-4.

S303-4: the agglutination rate is calculated based on the histogram prepared in step S303-3. First, the independent particles and aggregates are differentiated based on the histogram prepared in step S303-3. The detected particles are distributed to positions corresponding to the size of the carrier particles, that is, independent particles, two aggregate particles, and three aggregate particles. Actual particles are not distributed at locations smaller than independent particles, locations between the independent particles and two aggregate particles, locations between two aggregate particles and three aggregate particles, and locations larger than three aggregate particles, as indicated by v, w, x, and y in the FIG. 16. In this histogram, the threshold value is set between the forward scattered light intensity corresponding to the size of independent particles and the forward scatter light intensity corresponding to the size of two aggregate particles; and the number of independent particles (M) and the number of aggregate particles (P) can be calculated by identifying the particles distributed in the range below the threshold value as independent particles, and identifying the particles distributed within the range greater than the threshold value as aggregates. Furthermore, the total number of particles (T) can be determined by adding M and P, such that P/T can be calculated as the agglutination rate. Then, the process continues to step S303-5.

S303-5: The histogram prepared in step S303-3 and the data of the agglutination rate calculated in step S303-4 are stored in memory.

The aforesaid is shown in the flow chart of step S3 (standard solution measuring process). In this way the T1 standard solutions and T2 standard solutions are measured, and the agglutination rate is calculated for each standard solution.

S4 (Calibration Curve Preparation Process)

Figure 12:
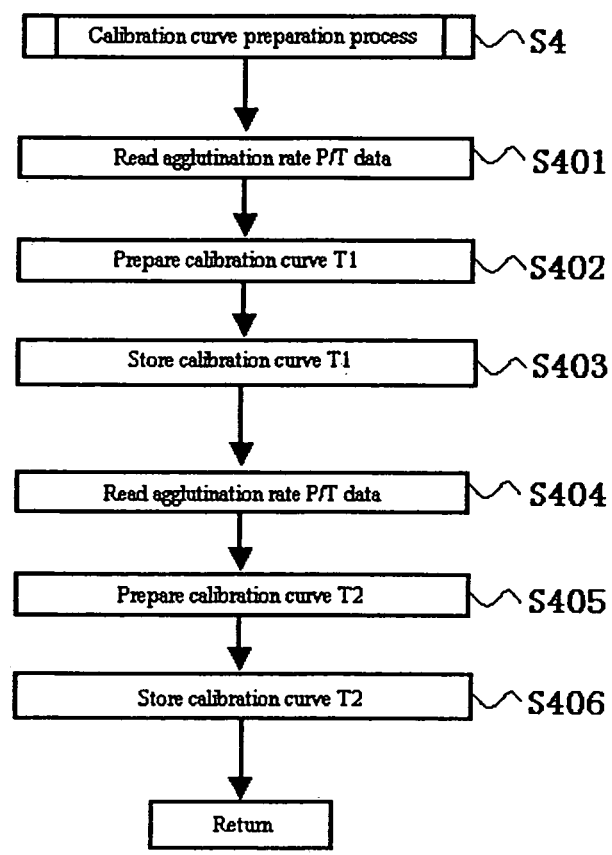
FIG. 12 illustrates the flow of the calibration curve preparing process in the embodiment of the present invention.

In step S4, the calibration curves are prepared based on the data of the agglutination rate for each standard solution obtained in step S3. The calibration curves prepared in step S4 include a calibration curve T1 prepared based on the data obtained by measurements performed at reaction time T1, and calibration curve T2 prepared based on data obtained by measurement performed at reaction time T2. The calibration curve T1 is prepared based on the concentration of the assay material in the T1 standard solutions input in step S1, and the agglutination rate obtained by measuring the T1 standard solutions in step S3. The calibration curve T2 is prepared based on the concentration of the assay material in the T2 standard solutions input in step S1, and the agglutination rate obtained by measuring the T2 standard solutions in step S3. The operation of the analysis program in the calibration curve preparation process is described below using the flow chart of FIG. 12. Each step of the flow chart is described below.

Step S401: Data of the concentration of the assay material in each T1 standard solution and agglutination rate of each T1 standard solution calculated in step S3 of the analysis are read from the memory unit 29. Then, the process continues to step S402.

S402: The calibration curve T1 is prepared based on the concentrations and agglutination rates. Then, the process continues to step S403.

S403: The calibration curve T1 prepared in step S402 is stored in memory. Then, the process continues to step S404.

S404: Data of the concentration of the assay material in each T2 standard solution and the agglutination rate of each T2 standard solution calculated in step S3 of the analysis are read from the memory unit 29. Then, the process continues to step S405.

S405: The calibration curve T2 is prepared based on the concentrations and agglutination rates. Then, the process continues to step S406.

S406: The calibration curve T2 prepared in step S405 is stored in memory.

The aforesaid steps are shown in the flow chart of the calibration curve preparation process. Thus, the calibration curve T1 and calibration curve T2 are prepared in this manner.

S5 ($\alpha$(T1) Setting Process)

In step S5, a threshold value $\alpha$(T1) is set for the agglutination rate at reaction time T1. In general, when calculating concentrations using a calibration curve, the concentration range in which the calculation of a reliable value is possible is a range in which the calibration curve is linear. For this reason, value have been determined based on the lower limit value of the range ensuring the linearity of the calibration curve T1 and the upper limit value of the range ensuring the linearity of the calibration curve T2, and have been stored as threshold value data in the memory unit 29. In the present step, the threshold value data are automatically read from the memory unit 29, and set as $\alpha$(T1). When $\alpha$(T1) is set in this way, the routine advances to step S6 (specimen mode selection determination).

S6 (Specimen Mode Selection Determination)

In step S6, a determination is made as to whether or not the specimen mode has been selected based on the measurement conditions input in the mode setting process of step S1. When [specimen mode] has been selected in step S1, the process continues to step S7 (specimen measuring process). When [specimen mode] is not selected in step S1, however, the process advances to step S9 (output process).

S7 (Specimen Measuring Process)

Figure 13:
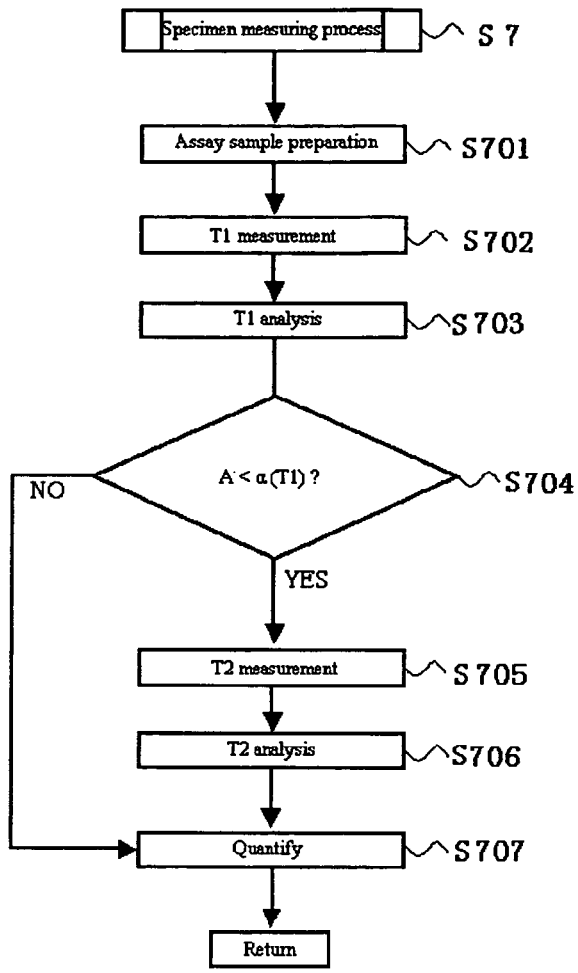
FIG. 13 illustrates the flow of the specimen measuring process in the embodiment of the present invention.
Figure 14:
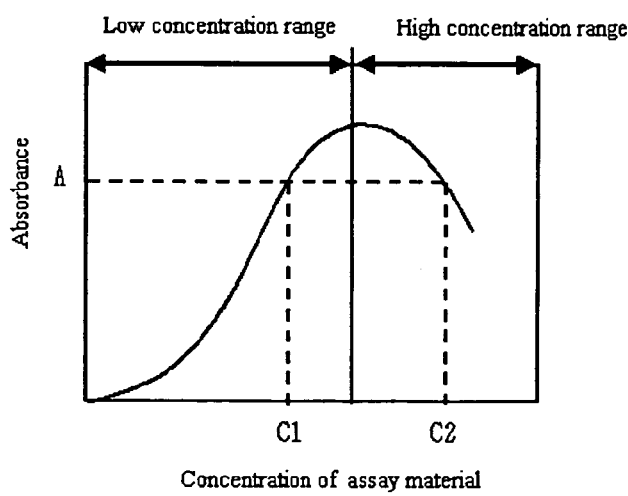
FIG. 14 is a chart showing the change in absorbance relative to the concentration of the assay material.
Figure 15:
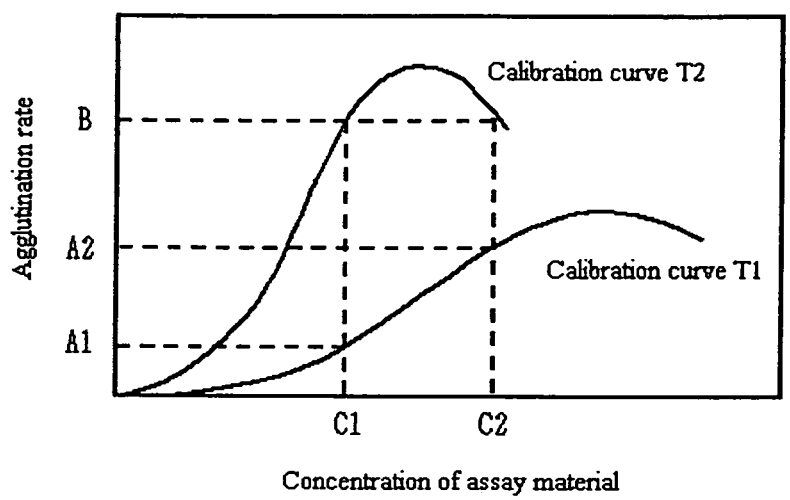
FIG. 15 shows an example of a calibration curve.

In the specimen measuring process, a specimen is measured, and the concentration of the assay material contained in the specimen is calculated based on the agglutination rate and the calibration curves prepared in step S4. FIG. 13 is a flow chart showing the flow of the specimen measuring process. In the specimen measuring process, step S701 (assay sample preparation), step S702 (T1 measurement), step S703 (T1 analysis), step S704 (determination whether to perform T2 measurement), step S705 (T2 measurement), step S706 (T2 analysis), and step S707 (quantification) are sequentially performed under the conditions input in the mode setting process of step S1.

S701 (Assay Sample Preparation)

The operation of the assay sample preparation unit 7 in the assay sample preparation process is described below referring to FIG. 3. The dispensing unit 12 first suctions specimen from the container placed in the specimen placement unit 8, and dispenses 10 μL of specimen into the container placed in the reaction unit 11. Then, the dispensing unit 12 suctions reaction buffer from the container placed in the reagent placement unit 10, and dispenses 80 μL to the container placed in the reaction unit 11. Then, the dispensing unit 12 suctions carrier suspension from the container 15 placed in the reagent placement unit 10, and dispenses 10 μL to the container placed in the reaction unit 11. The antigen-antibody reaction is started by the addition of the carrier particle suspension. The assay sample in the container in the reaction unit 11 is agitated while maintained at a temperature of 45° C. Then, the fluid delivery device 13 suctions 14.5 μL of the assay sample in the container in the reaction unit 11, and delivers the assay sample to the sheath flow cell 19 of the measuring unit 6. When the assay sample is suctioned from the container in step S702, the reaction unit 11 thereafter continues to agitate the assay sample in the container while maintaining it at a temperature of 45° C.

S702 (T1 Measurement)

In step S702, the forward scattered light signal is detected at reaction time T1 input in step S1. When the reaction time T1 input in step S1 is, for example, 20 seconds, then the operation of the assay sample preparation unit 7 and the measuring unit 6 is controlled by the control program so as to detect the forward scattered light 20 seconds after the start of the antigen-antibody reaction. The operation of the measuring unit 6 in step S702 is identical to the operation in step S302 (measuring process), that is, the forward scattered light signals are detected and the detected signals are stored in the memory unit 29.

S703 (T1 Analysis)

When the forward scattered light is detected in step S702, T1 analysis is executed by the analyzing unit 30 based on the analysis program. The operation of the analysis program in step S703 is identical to the operation in step S303 (analysis process), that is, the agglutination rate A is calculated based on the detected forward scattered light signals. Then, the data of the calculated agglutination rate A and the prepared histogram are stored in the memory unit 29.

S704 (Determination of Whether to Perform T2 Measurement)

The agglutination rate A calculated in step S703 is compared to the threshold value α(T1) set in step S5. When the value of the calculated agglutination rate A is greater than α(T1), a measurement at reaction time T2 is not required because it is possible to determine the assay material concentration using the agglutination rate A at reaction time T1. In this case, therefore, the temperature maintenance and agitation in the container of the reaction unit 11 ends in the assay sample preparation unit 7, and the process advances to step S707. When the value of the calculated agglutination rate A is less than α(T1), a measurement at reaction time T2 is required because it is impossible to determine the assay material concentration using the agglutination rate A at reaction time T1. At this time, therefore, the process advances to step S705. Also at this time, the temperature maintenance and agitation in the reaction unit 11 is continued thereafter as before until reaction time T2.

S705 (T2 Measurement)

When the value of the agglutination rate A is less than α(T1) in step S704, the next step S705 is executed. In step S705, the forward scattered light signal is detected at reaction time T2 input in step S1. When the reaction time T2 input in step S1 is, for example, 15 minutes, then the operation of the assay sample preparation unit 7 and the measuring unit 6 is controlled by the control program so as to detect the forward scattered light 15 minutes after the start of the antigen-antibody reaction. The operation of the measuring unit 6 in the T2 measurement is identical to the operation in step S302 (measuring process), that is, the forward scattered light signals are detected and the detected signals are stored in the memory unit 29.

S706 (T2 Analysis)

When the forward scattered light is detected in step S705, T2 analysis is executed by the analyzing unit 30 based on the analysis program. The operation of the analysis program in step S706 is identical to the operation in step S303 (analysis process), that is, the agglutination rate B is calculated based on the detected forward scattered light signals, and the data of the calculated agglutination rate B and the prepared histogram are stored in the memory unit 29.

S707 (Quantification)

In step S707, the concentration of assay material contained in the specimen is calculated based on the calibration curves preciously prepared in step S4 and the agglutination rate obtained in step S703 or S706. When the T2 measurement and T2 analysis are not performed, the concentration of the assay material is calculated based on the calibration curve T1 and the agglutination rate A at reaction time T1. However, when the T1 measurement and T2 analysis are performed, the concentration of the assay material is calculated based on the calibration curve T2 and the agglutination rate B at reaction time T2. Then, the concentration data calculated in step S707 is stored in the memory unit 29.

S8 (All Specimens Completed)

When a plurality of specimens are assayed, step S7 is repeated until [measurement of all specimens has been completed] has been determined in step S8. When the measurement of all specimens has been completed, the process advances to step S9.

S9 (Output Process)

The standard solution agglutination rate data stored in step S3, the calibration curve data stored in step S4, and specimen agglutination rate and concentration data stored in step S7 are output and displayed on the liquid crystal touch panel 2.

The aforesaid steps are shown in the flow chart of the general control in the present embodiment. As described above, the biological sample analyzing apparatus 1 is an automatic analyzer that performs automatically from the preparation of the assay sample to the quantification of the assay material.

(Measurement Example 1)

The example describes the preparation of calibration curves using the previously described biological sample analyzing apparatus 1. The reaction time were set at T1=20 seconds, and T2=15 minutes.

A latex reagent containing latex particle on which anti-CRP antibody is immobilized was used as the carrier particle suspension. This reagent was prepared by the following method. First, 50 μl of 10% (w/v) polystyrene latex (commercial product) was added to 450 μl of GTA buffer solution (0.53 mg/ml 3,3-dimethylglutaric acid, 0.4 mg/ml trishydroxymethylaminomethane, 0.35 mg/ml 2-amino-2-methyl-1,3-propane diol; pH 7.0) containing 100 μg of anti-CRP antibody (mouse monoclonal antibody, a commercial product), and allowed to rest for 2 hours. The solution was centrifuged for 10 minutes at 10,000×g, and 1 ml GTA buffer solution containing 1% (w/v) bovine serum albumin (commercial product) was added to the centrifuge precipitate, then the solution was subjected to an ultrasound process for dispersion. The process from centrifuging to dispersion was repeated a plurality of times, and the supernatant was removed after the final centrifugation, and 1 ml GTA buffer solution (pH 6.2) containing 220 mg/ml glycerin and 0.3% (w/v) bovine serum albumin was added and subjected to ultrasound processing. The solution was used as the latex reagent. A suitable size of the carrier particles in the present embodiment is a particle diameter ranging from 0.1~1.0 μm. The particle diameter of the polystyrene latex used in the present example was 0.7 μm.

The reaction buffer solution was prepared as follows. The prepared reaction buffer solution contained 1.6 mg/ml 3,3-dimethylglutaric acid, 1.1 mg/ml 2-amino-2-methyl-1,3-propane diol, 18.18 mg/ml trishydroxymethyl aminomethane, 0.5% (w/v) bovine serum albumin, with pH 6.7.

The standard solutions were prepared by the following method. A PBS solution (2.4 mg/ml trishydroxymethylamino methane, 2.4 mg/ml sodium chloride; pH 7.5) containing 5% (w/v) bovine serum albumin was prepared, and purified CRP (commercial product) was added to produce concentrations of $4.05 \times 10^2$, $1.215 \times 10^3$, $5 \times 10^3$, $2 \times 10^4$, $6 \times 10^4$, $1.8 \times 10^5$, and $3 \times 10^5$ ng/mL as the T1 standard solutions, and purified CRP (commercial product) was added to produce concentrations of 5, $15 \times 10$, $4.5 \times 10$, $1.35 \times 10^2$, $4.05 \times 10^2$, $1.215 \times 10^3$ ng/mL as the T2 standard solutions.

Figure 17A:
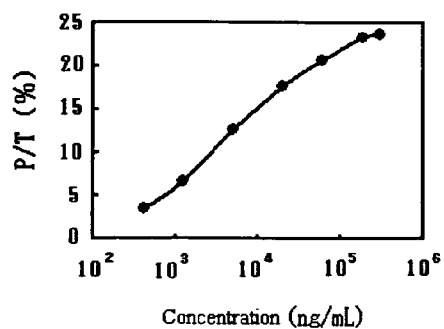
FIG. 17A shows a calibration curve at reaction time T1 obtained by measurement example 1 of the embodiment of the present invention.
Figure 17B:
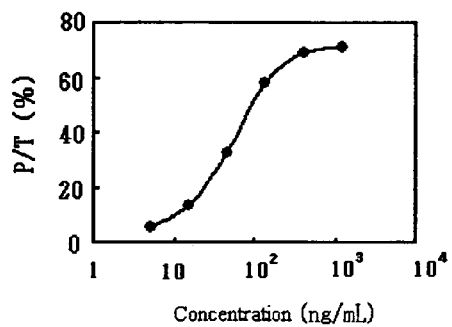
FIG. 17B shows a calibration curve at reaction time T2 obtained by measurement example 1 of the embodiment of the present invention.

FIG. 17 shows the calibration curves obtained by measuring the T1 and T2 standard solutions. FIG. 17A is a calibration curve obtained by measuring the agglutination rate of the T1 standard solutions at a reaction time of 20 seconds. FIG. 17B is a calibration curve obtained by measuring the agglutination rate of the T2 standard solutions at a reaction time of 15 minutes. In both cases, the agglutination rate is plotted on the vertical axis, and the CRP concentration is plotted on the horizontal axis.

When the calibration curve T1 is used, it can be understood from FIG. 17A that CRP can be measured in a measurement range of 4×10² ng/mL to 3×10⁵ ng/mL. When the calibration curve T2 is used, it can also be understood from T2 in FIG. 17 that CRP concentration can be measured in a measurement range from 5 ng/mL to 1×10³ ng/mL. From the above information it can be understood that, in the biological sample analyzing apparatus 1, CRP concentration can be measured in an extremely broad measurement range from 5 ng/mL to 3×10⁵ ng/mL by using both calibration curve T1 and calibration curve T2.

(Measurement Example 2)

Next, the calibration curve T2 was prepared at various reaction times T2 using the previously described biological sample analyzing apparatus 1.

Each type of reagent and the T2 standard solutions used in the present example were identical to the reagents and T2 standard solutions used in measurement example 1.

Figure 18:
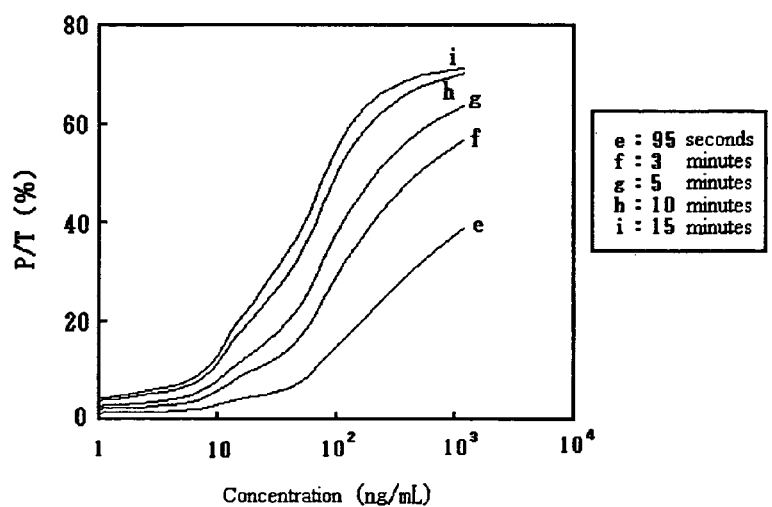
FIG. 18 shows a calibration curve obtained by measurement example 2 of the embodiment of the present invention.

FIG. 18 shows the calibration curve T2 at each reaction time. These calibration curves T2 are calculated at reaction time T2 of 95 sec, 3.0 min, 5.0 min, 10.0 min, and 15.0 min; curve e is 95 sec, f is 3.0 min, g is 5.0 min, h is 10.0 min, and i is 15.0 min.

In FIG. 18, the change in the agglutination rate per unit concentration increases in conjunction with the lengthening of reaction time T2. In this way the agglutination rate sensitivity becomes greater as the time set as the reaction time T2 increases. That is, effective measurement is possible by setting the reaction time T2 in accordance with the measurement range required by the operator without increasing the reaction time longer than is necessary.

Moreover, it is understood that the calibration curve e in FIG. 18 describes an increasing agglutination rate in conjunction with an increase in CRP concentration in the concentration range from 10 ng/mL to 1×10³ ng/mL. In this way even when the reaction time T2 was set at a short 95 seconds, the measurement could be used in the calibration curve, and in this case CRP was measurable even in specimens with a relatively low concentration of 10 ng/mL.

(Measurement Example 3)

The measurement results shown were taken when the reaction time T1 was set at 20 sec, and reaction time T2 was set at 95 sec, using the previously described biological sample analyzing apparatus 1. In the present example, the agglutination rate threshold value $\alpha(T1)$ was set at 7%. In this way the concentration of CRP contained in a specimen could be calculated based on the agglutination rate A and calculation curve T1 at reaction time T1 when the agglutination rate A was 7% or greater. Moreover, the concentration of CRP contained in a specimen could be calculated based on the agglutination rate B at reaction time T2 when the agglutination rate A was less than 7%.

Each type of reagent and standard solutions used in the present example were identical to the reagents and standard solutions used in measurement example 1. In the present example, blood plasma 1~5 and blood sera 1~3 containing various concentrations of CRP are used as specimens. The same specimens were assayed using a Dimension R×L automatic bioanalyzer, manufactured by Dade Behring, Inc., to determine the concentration of CRP contained in each specimen.

Table 1 shows the results when each specimen was measured using the biological sample analyzing apparatus 1. Among the categories of Table 1, [A (%)] are values representing the agglutination rate A (%) at reaction time T1, and [B (%)] are values representing the agglutination rate B (%) at reaction time T2. The [calibration curve] represents the calibration curve used to calculate the concentration, T1 indicating that the calibration curve T1 was used, and T2 indicating that the calibration curve T2 was used. Furthermore, [concentration I] represents the CRP concentration (ng/mL) obtained using the biological sample analyzing apparatus 1, and [concentration II) represents the CRP concentration obtained using Dimensional R×L.

TABLE 1

| Specimen | A (%) | B (%) | Calibration curve | Concentration I (ng/mL) | Concentration II (ng/mL) |
|---|---|---|---|---|---|
| Plasma 1 | 1.95 | 18.48 | T2 | 16 | 0 |
| Plasma 2 | 3.22 | 30.22 | T2 | 46 | 100 |
| Plasma 3 | 11.23 | — | T1 | $3.5 \times 10^3$ | $3 \times 10^3$ |
| Plasma 4 | 21.17 | — | T1 | $4.96 \times 10^4$ | $5 \times 10^4$ |
| Plasma 5 | 25.11 | — | T1 | $2.73 \times 10^5$ | $2.4 \times 10^5$ |
| Serum 1 | 2.06 | 23.76 | T2 | 29 | 0 |
| Serum 2 | 20.34 | — | T1 | $3.9 \times 10^4$ | $3.3 \times 10^4$ |
| Serum 3 | 22.91 | — | T1 | $1.26 \times 10^5$ | $1 \times 10^5$ |

It can be understood from Table 1 regarding the specimens having relatively high concentrations of CRP (plasma 3, plasma 4, plasma, 5, serum 2, serum 3) that the CRP concentrations calculated from assays using the biological sample analyzing apparatus 1 approximate the CRP concentrations determined beforehand in assays using the Dimension R×L. In regard to the specimens with relatively low concentrations of CRP (plasma 1, plasma 2, and serum 1), however, the assays using the biological sample analyzing apparatus 1 calculated CRP concentrations of higher sensitivity than did the assays using the Dimension R×L.

(Measurement Example 4)

The measurement results in this case sows the results when whole blood was assayed using the previously described biological sample analyzing apparatus 1. The whole blood further contained hemocytes. Therefore, when whole blood is used as the specimen and the same quantity is used as when assaying serum and plasma, the assay values are lower because they reflect the hemocyte component (hemocyte volume). Therefore, the hemocyte volume must be compensated when assaying whole blood. In the present example, this compensation is made using the method disclosed in U.S. Application Patent Publication No. 2003-0082662. Specifically, whole blood specimens were assayed using a completely automated hemocyte analyzer model XE-2100 manufactured by Sysmex Corporation to determine the number of hemocytes beforehand. Compensation was accomplished using the following equation.

$$C = C0 / \{1 - (B/A)\}$$

(Where C represents the concentration of assay material after compensation, C0 represents the concentration of the assay material when whole blood is measured, B represents the number of hemocytes contained in the whole blood, and A represents a constant.) The constant A can be determined experimentally from the correlation between the number of hemocytes and the hematocrit value. The hematocrit value is equivalent to the total number of hemocytes when the hematocrit is assumed to be 100% (that is, when the entire whole blood sample is the hemocyte component); since red blood cells comprise nearly all the hemocytes in whole blood, the hematocrit value can be used as the percentage volume of hemocytes present in a constant amount of whole blood. The constant A is equivalent to the total number of hemocytes when the hematocrit value is assumed to be 100% (that is, the hemocyte component is the entire whole blood sample). The percentage hemocyte component in the collected whole blood sample can be determined by calculating B/A.

In the present example, reaction time T1=20 seconds, T2=95 seconds, and threshold value α(T1) was set at 7%. The reagents and standard solutions used were identical to the reagents and standard solutions used in measurement example 1. The specimens included whole blood 1~4 containing various concentrations of CRP, and plasma 1~4 obtained by centrifuging the whole blood 1~4 (8,000 rpm for 5 minutes).

Table 2 shows the results obtained when each specimen was measured suing the biological sample analyzing apparatus 1. In Table 2, the [calibration curve] represents the calibration curve used to calculate the concentration, T1 indicating that the calibration curve T1 was used, and T2 indicating that the calibration curve T2 was used. Furthermore, [concentration] represents the CRP concentration (ng/mL) obtained using the biological sample analyzing apparatus 1.

TABLE 2

| Specimen | Calibration curve | Concentration (ng/mL) |
|---|---|---|
| Whole blood 1 | T2 | 250 |
| Whole blood 2 | T2 | 510 |
| Whole blood 3 | T1 | $7.39 \times 10^3$ |
| Whole blood 4 | T1 | $2.28 \times 10^4$ |
| Plasma 1 | T2 | 260 |
| Plasma 2 | T2 | 490 |
| Plasma 3 | T1 | $8.33 \times 10^3$ |
| Plasma 4 | T1 | $2.32 \times 10^4$ |

When the CRP concentrations of whole blood 1 and plasma 1, whole blood 2 and plasma 2, whole blood 3 and plasma 3, whole blood 4 and plasma 4 were compared, in each case the whole blood CRP concentration approximated the plasma CRP concentration. This indicated that whole blood could be used for measurements.

In the present embodiment, measurements were performed at different reaction times (reaction time T1 and reaction time T2). When the relationship of reaction time T1 and reaction time T2 was T1<T2, the reaction was relatively more stable at reaction time T2 than reaction time T1. Therefore, the measurement of the relatively stable reaction at reaction time T2 has better sensitivity and reproducibility than the measurement of the relatively unstable reaction at reaction time T1. The reason for this difference is that the calibration curve T2 at reaction time T2 was used to calculate the particularly low concentration of the assay material. However, the measurement at reaction time T1 was less affected by the zone phenomenon than the measurement at reaction time T2. The reason for this difference is that the calibration curve T1 at reaction time T1 was used to calculate the particularly high concentration of the assay material.

In the present embodiment, predetermined conditions are provided relating to the measurement results at reaction time T1, such that the calibration curve T1 is used when calculating the concentration of assay material that has a high concentration, and the calibration curve T2 is used when calculating the concentration of assay material that has a low concentration. For this reason, measurements at both the first reaction time (reaction time T1) and the second reaction time (reaction time T2) are not always necessary, and measurement at reaction time T2 is performed only when the measurement results for reaction time T1 do not meet predetermined conditions. In this way the efficiency of the measurement is improved.

In the present embodiment, the reaction time T1 and reaction time T2 can be set in accordance with the measurement range deemed necessary by the operator. In this way measurement can be performed efficiently without performing measurements longer than necessary.

Although the reaction time T1 is set at 10 seconds, and the reaction time T2 is set at either 95 seconds or 15 minutes in the present embodiment, the reaction time T1 and reaction time T2 are not limited to these times. The time of the reaction time T1 and the reaction time T2 differ depending on the assay material. For this reason, the times of the reaction time T1 and the reaction time T2 are set at times suitable for the material being measured.

The biological sample analyzing apparatus 41 of another embodiment of the present invention is described below. The biological sample analyzing apparatus 41 employs the immunoturbidity method using latex particles as the measurement principle.

Figure 19:
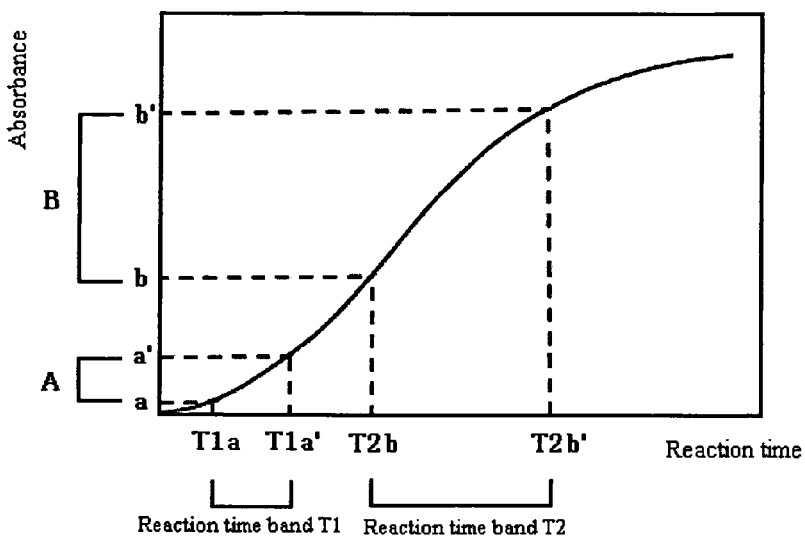
FIG. 19 shows the change in absorbance relative to reaction time in another embodiment of the present invention.

The biological sample analyzing apparatus 41 first prepares an assay sample by mixing a carrier particle suspension and reaction buffer solution with a specimen, such as blood, urine or the like. Then, the prepared assay sample is irradiated with light, the light transmitted through the assay sample is detected, and the absorbance is determined based on the detected transmitted light. FIG. 19 shows an example of the change in absorbance during the reaction time. The biological sample analyzing apparatus 41 detects the absorbance at reaction times T1$a$ and T1$a$', and calculates the amount of change A in absorbance (A=a'−a) during the reaction time span T1 based on each absorbance (a, a') measurement. Then, the value of the amount of change A is compared to a predetermined threshold value, and a determination is made as to whether or not to perform measurements during reaction time span T2. When the amount of change A exceeds the predetermined threshold value, the assay material contained in the specimen is quantified based on the amount of change A without performing measurements at reaction time span T2. When the amount of change A is less than the predetermined threshold value, measurements are performed during the reaction time span T2 to obtained measurement results of higher reliability since the measurement results in reaction time span T1 have low reliability. In this case, the absorbance is detects at reaction times T2$b$ and T2$b$', and the amount of change B in the absorbance during the reaction time span T2 is calculated (B=b'−b) based on the detected absorbances (b, b'). Then, the assay material is quantified based on the amount of change B.

(General Structure of Biological Sample Analyzing apparatus 41)

An external view of the biological sample analyzing apparatus 41 provides a liquid crystal touch panel, assay sample preparation unit cover, and start switch similar to the biological sample analyzing apparatus 1 shown in FIG. 1. The internal structure of the biological sample analyzing apparatus 41 has a controller, measurement unit, and assay sample preparation unit similar to the biological sample analyzing apparatus 1 shown in FIG. 2.

(Structure of the Assay Sample Preparation Unit)

Figure 20:
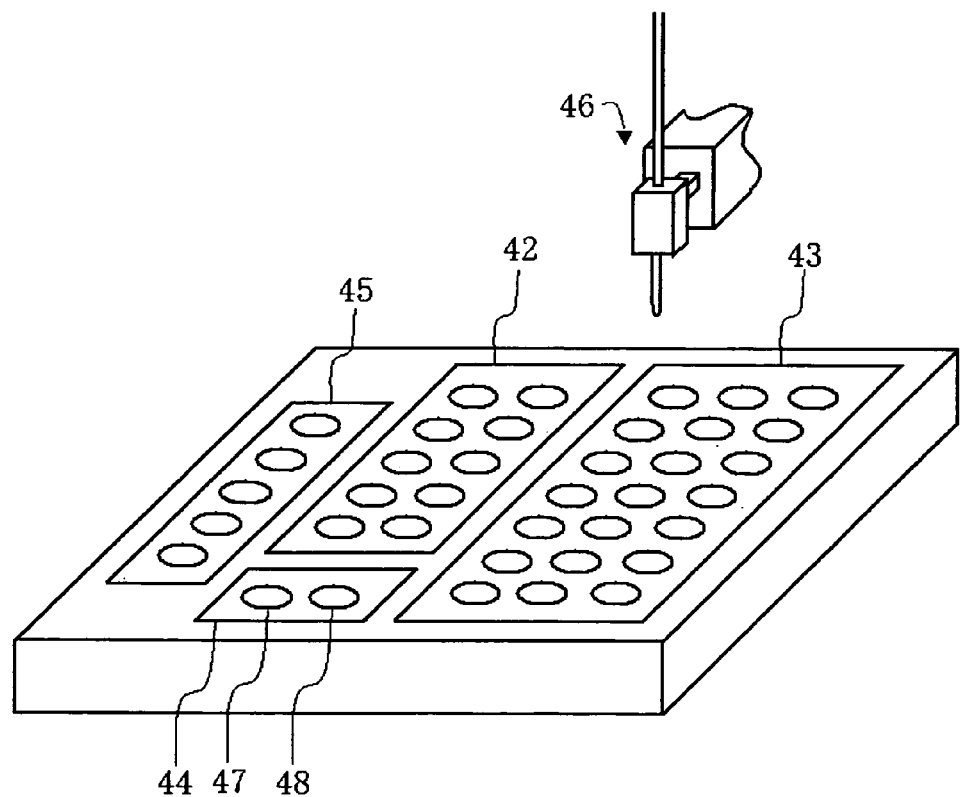
FIG. 20 shows the assay sample preparation unit of another embodiment of the biological sample analyzing apparatus of the present invention.

FIG. 20 shows the assay sample preparation unit of the biological sample analyzing apparatus 41. The assay sample preparation unit includes a specimen placement unit 42, standard solution placement unit 43, reagent placement unit 44, reaction unit 45, and dispensing unit 46. The operator places a container containing the specimen in the specimen placement unit 42 by opening the cover of the assay sample preparation unit. The operator respectively places a containers of standard solution in the standard solution placement unit 43. The operator respectively places a container 47 containing reaction buffer and container 48 containing carrier particle suspension in the reagent placement unit 44. A light-transmitting container is placed in the reaction unit 45, and the assay sample is prepared by mixing the reaction buffer and carrier particle suspension with the specimen or standard solution. Although not shown in the drawing, the reaction unit 45 is provided with a temperature controlling mechanism for maintaining the solution in the container at a constant temperature, and a mixing mechanism for agitating the solution in the container. The dispensing unit 46 suctions and dispenses a predetermined amount of fluid from the tip, and the unit is movable vertically, laterally, and back-and-forth by means of a drive device not shown in the drawing.

(Structure of the Measuring Unit)

Figure 21:
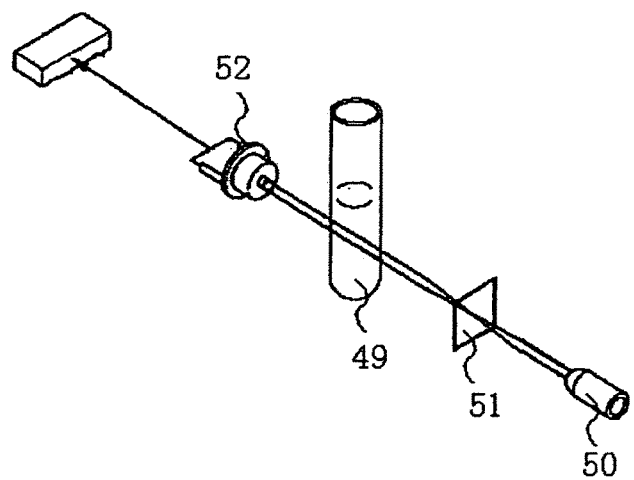
FIG. 21 shows the measurement unit of another embodiment of the biological sample analyzing apparatus of the present invention.

FIG. 21 shows the measuring unit. The measuring unit is provided with a container 49, light source 50, filter 51, and photodiode 52. The light from the light source 50 is diffracted into a spectrum at 800 nm by the filter 51. The diffracted light passes through the assay sample in the container 49, and the transmitted light reaches the photodiode 52. The photodiode 52 subjects the received transmitted light to photoelectric conversion, which is output as electrical signals. The output signals are transmitted to the controller.

(Structure of the Controller)

The structure of the controller of the biological sample analyzing apparatus 41 includes a central processing unit (CPU), microcomputer provided with storage devices such as ROM, RAM and the like, and circuits for processing the signals sent from the measuring unit. The Controller functions as an analysis unit and operation controller. The memory unit stores an analysis program for analyzing the signals obtained from the particles in the sample, and a control program for controlling the operation of each unit. The memory unit further stores the data of the signals detected by the measuring unit, and processing results of the analysis program. The analysis unit analyzes the signals detected by the measuring unit based on the analysis program, and generates data. The data generated by the analysis unit are output to the liquid crystal touch panel. The operation controller controls the operation of each unit based on the control program stored in the memory unit.

The operation of the biological sample analyzing apparatus 41 is described in detail below. First, the operator places standard solutions, specimens, and reagents at the predetermined positions in the assay sample preparation unit. The standard solutions include standard solutions used for reaction time T1 and standard solutions used for reaction time T2, and the plurality of standard solutions have graduatedly different concentrations of included assay material. Then, the standard solutions can be placed in the standard solution placement unit 43 of the assay sample preparation unit shown in FIG. 20 by opening the cover of the assay sample preparation unit of the apparatus 41. The specimen can be placed in the specimen placement unit 42 of the assay sample preparation unit. Furthermore, the container 47 containing reaction buffer and the container 48 containing carrier particle suspension can be respectively placed in the reagent placement unit 44 of the assay sample preparation unit.

Figure 22:
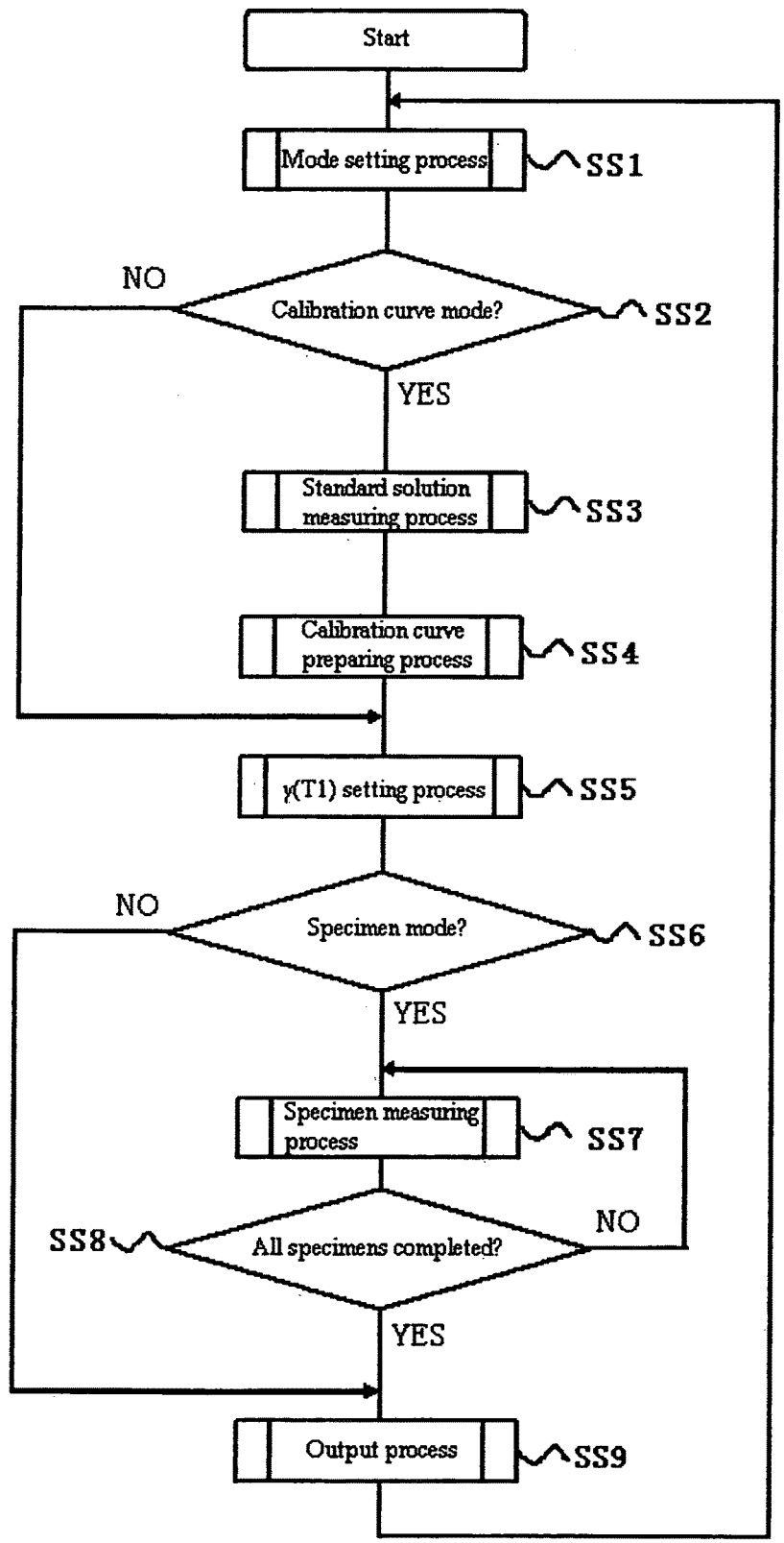
FIG. 22 illustrates the flow of the overall control of another embodiment of the biological sample analyzing apparatus of the present invention.

FIG. 22 is a flow chart showing the general control flow of the control program. In step SS1 (mode setting process), a condition setting screen is displayed on the liquid crystal touch panel. In the biological sample analyzing apparatus 41, there are two measurement modes, which include the a calibration curve mode for measuring the standard solutions and preparing calibration curves, and a specimen mode for measuring a specimen and quantifying the assay material contained in the specimen; each mode is selectable by the operator in accordance with the measurement to be performed. The operator enters various settings in the displayed condition setting screen, for example, the measurement mode, reaction time which is time from the start of the antigen-antibody reaction by the addition of the carrier particle suspension until agglutination is detected, concentrations of the assay material contained in each standard solution and the like. When setting input of step SS1 ends, step SS2 (discrimination of the calibration curve mode selection), step SS3 (standard solution measuring process), step SS4 (calibration curve preparation process), step SS5 ($\gamma$(T1) setting process), step SS6 (discrimination of the specimen mode selection), step SS7 (specimen measuring process), step SS8 (all specimens completion), and step SS9 (output process) are sequentially executed.

The assay sample preparation unit, measuring unit, and analysis unit are controlled by the control program, and the sequential operations of steps SS1 to SS9 are performed automatically. Each step is described below.

SS1 (Mode Setting Process)

Figure 23A:
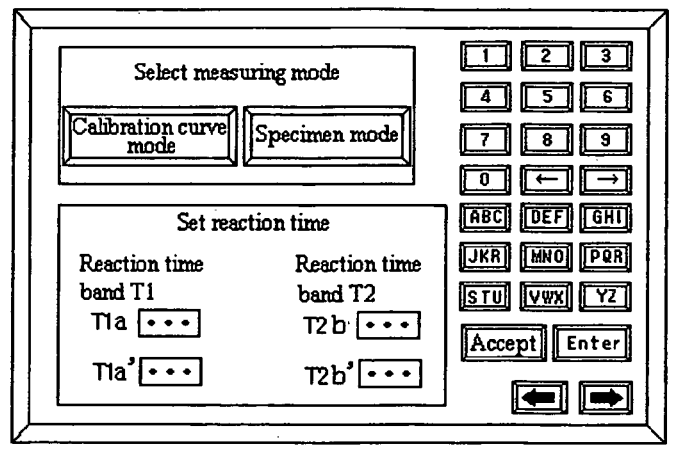
FIG. 23A shows an example of a measurement setting screen displayed on a liquid crystal touch panel of another embodiment of the biological sample analyzing apparatus of the present invention.
Figure 23B:
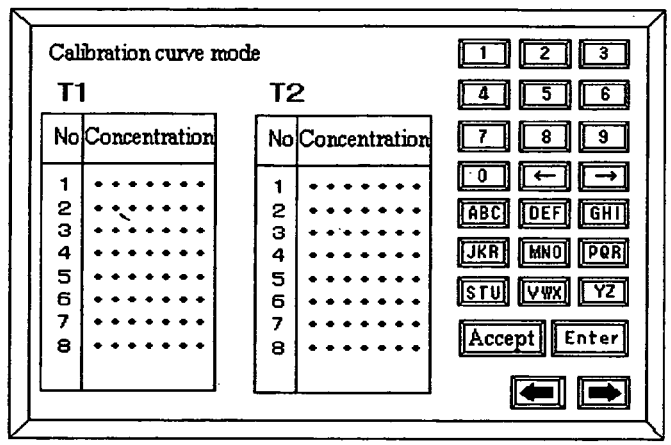
FIG. 23B shows an example of a measurement setting screen displayed on a liquid crystal touch panel of another embodiment of the biological sample analyzing apparatus of the present invention.
Figure 23C:
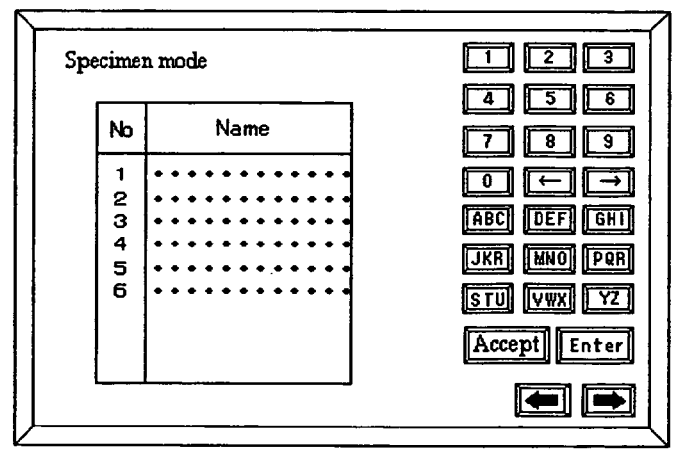
FIG. 23C shows an example of a measurement setting screen displayed on a liquid crystal touch panel of another embodiment of the biological sample analyzing apparatus of the present invention.
Figure 24:
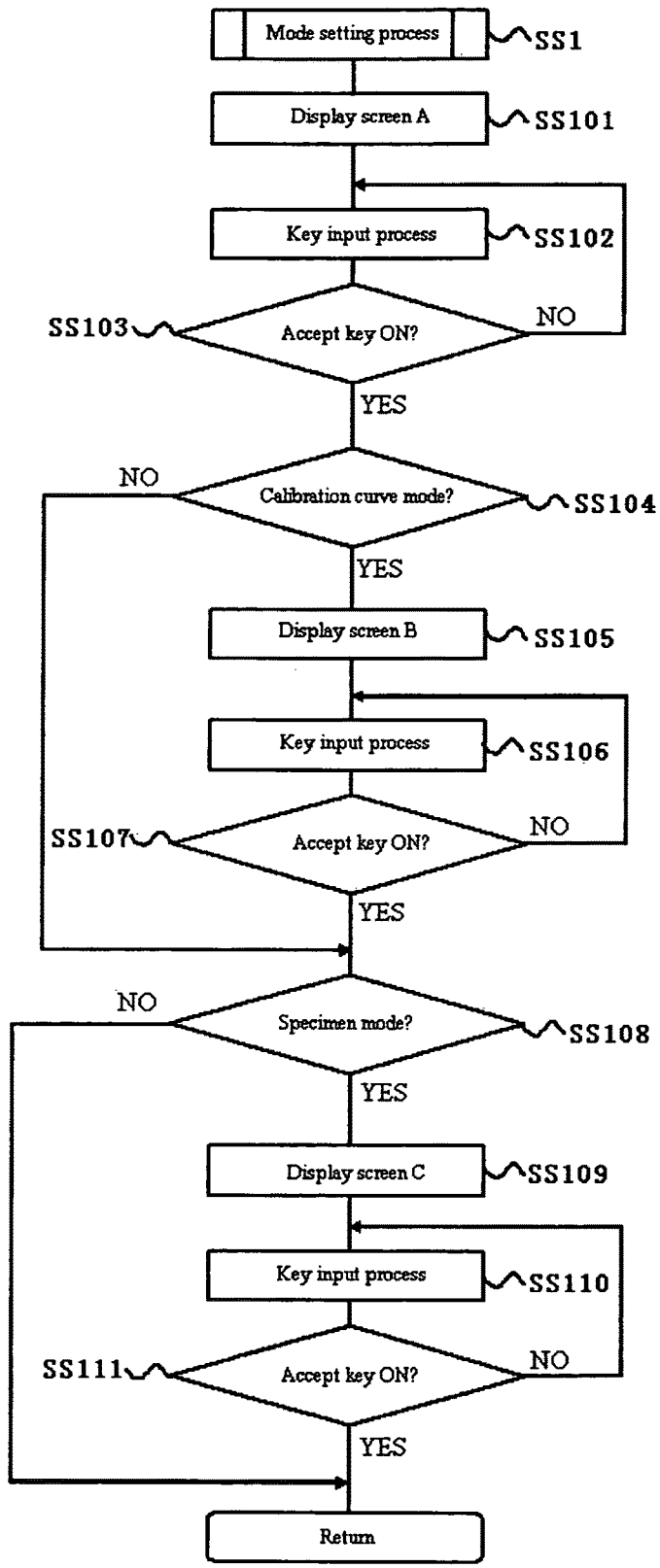
FIG. 24 illustrates the flow of the mode setting process in another embodiment of the present invention.

The mode setting process in the biological sample analyzing apparatus 41 is described below with reference to FIGS. 23 and 24. FIG. 23 shows the screen displayed on the liquid crystal touch panel during the mode setting process. Various types keys are displayed on the screens, and a key is selected when the operator uses a finger or the like to touch a position at which a key is displayed on the liquid crystal touch panel 2. FIG. 24 is a flow chart showing the flow of the mode setting process. Each step of the flow chart is described below.

SS101: The screen A shown in FIG. 23A is displayed on the liquid crystal touch panel. The process then advances to step SS102.

SS102: The measurement mode and reaction time setting inputs are received on the screen A. A key for operator selection of the measurement mode is provided at the upper left side of the screen A. Calibration curves are prepared when the [calibration curve mode] key is selected, and a specimen is measured when the [specimen mode] key is selected. Furthermore, when both the [calibration curve mode] key and the [specimen mode] key are selected, the specimen is measured after the calibration curves have been prepared. Boxes for the operator to enter the reaction times T1 and T2 are provided in the lower left of the screen A. The biological sample analyzing apparatus 41 determines the change in absorbance during the reaction time span T1 from reaction time T1$a$ to reaction time T1$a'$, and determines the change in absorbance during reaction time span T2 from reaction time T2$a$ to reaction time T2$a'$. Therefore, boxes for setting the reaction times are provided at four locations T1$a$, T1$a'$, T2$a$, and T2$a'$. A ten-key pad is provided on the right side of the screen A for entering numerical values in each box. When setting input on screen A has been completed, the process moves to step SS103.

SS103: An [Accept] key is displayed on the screen A, and the selection of the [Accept] key by the operator is received in step SS103. When the [Accept] key has been selected, the process continues to step SS104.

SS104: When [calibration mode] is selected in step SS102, the process continues to step SS105. However, when [calibration mode] is not selected in step SS102, the process advances to step SS108.

SS105: The screen B shown in FIG. 23B is displayed on the liquid crystal touch panel. Then, the routine advances to step SS106.

SS106: The setting inputs related to the calibration curve mode, such as the number and concentrations of each standard solution used to prepare the calibration curves, are received on the screen B. Boxes for the operator to enter the number and concentrations of each standard solution are provided on the left side of the screen B. A ten-key pad is provided on the right side of the screen B for entering numerical values in each box. When setting input on screen B has been completed, the process moves to step SS107.

SS107: The [Accept] key is displayed on the screen B, and the operator selection of the [Accept] key is received in step SS107. When the [Accept] key has been selected and pressed on screen B, the process continues to step SS108.

SS108: When the [specimen mode] is selected in step SS102, the process continues to step SS109. When the [specimen mode] has not been selected in step SS102, however, the mode setting process ends.

SS109: The screen C shown in FIG. 23C is displayed on the liquid crystal touch panel. Then, the routine advances to step SS110.

S110: Setting inputs related to the specimen mode, such as specimen number and specimen name and the like, are received on screen C. Boxes for the operator to enter the number and name of each specimen are provided on the left side of the screen C. A ten-key pad is provided on the right side of the screen C for entering numerical values and text in each box. When setting input on screen C has been completed, the process moves to step SS111.

SS111: The [Accept] key is displayed on the screen C, and the operator selection of the [Accept] key is received in step SS111. When the [Accept] key has been selected, the mode setting process ends.

SS2 (Calibration Mode Selection Determination)

In step SS2, a determination is made as to whether or not the calibration mode has been selected based on the measurement conditions input in the mode setting process of step SS1. When [calibration mode] has been selected in step SS1, the process continues to step SS3 (standard solution measuring process). When [calibration mode] is not selected in step SS1, however, the process advances to step SS5 ($\gamma$T1) setting process).

SS3 (Standard Solution Measuring Process)

Figure 25:
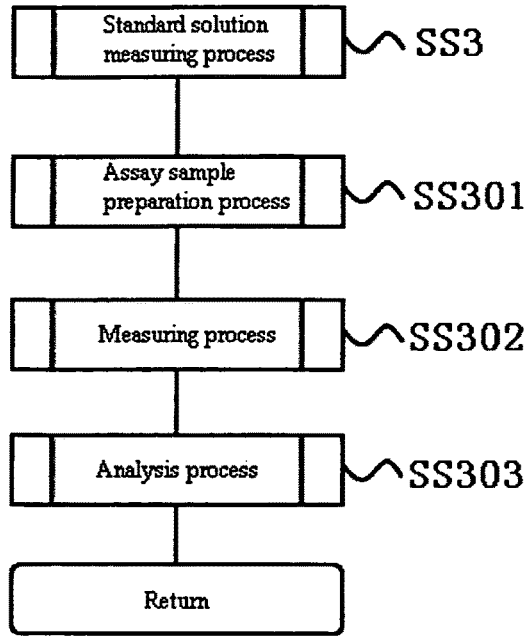
FIG. 25 illustrates the flow of the standard fluid measuring process in another embodiment of the present invention.

In step SS3, the standard solutions containing known concentrations of assay material are measured. FIG. 25 is a flow chart showing the flow of the standard solution measuring process. In the standard solution measuring process, step SS301 (assay sample preparation process), step SS302 (measuring process), and step SS303 (analysis process) are sequentially performed. Steps SS301, SS302, and SS303 are described below.

SS301 (Assay Sample Preparation Process)

The operation of the assay sample preparation unit in step SS301 is described referring to FIG. 20. First, the dispensing unit 46 suctions standard solution from the container placed in the standard solution placement unit 43, and dispenses 15 µL to the container placed in the reaction unit 45. Then, the dispensing unit 46 suctions reaction buffer from the container placed in the reagent placement unit 44, and dispenses 140 µL to the container placed in the reaction unit 45. Then, the dispensing unit 46 suctions carrier suspension from the container 48 placed in the reagent placement unit 44, and dispenses 50 µL to the container placed in the reaction unit 45. The antigen-antibody reaction is started by the addition of the carrier particle suspension. The assay sample in the container in the reaction unit 45 is agitated while maintained at a temperature of 37° C.

When preparing a calibration curve, a plurality of standard solutions are used which have graduatedly different concentrations of included assay material. Therefore, a plurality of T1 standard solutions and T2 standard solutions are placed in the standard solution placement unit 43. Then, assay samples are sequentially prepared from the standard solutions of each concentration placed in the standard solution placement unit 43. Thus, when assay samples are prepared from the standard solutions, the subsequent steps SS302 and SS303 described later are sequentially executed. Then, using the assay samples prepared from the T1 standard solutions, the absorbance a at reaction time T1$a$ and the absorbance a' at reaction time T1$a$' are calculated, and the amount of change A in absorbance (A=a'−a) during the reaction time span T1 is calculated based on the absorbances a and a'.

Then, using the assay samples prepared from the T2 standard solutions, the absorbance b at reaction time T2$b$ and the absorbance b' at reaction time T2$b$' are calculated, and the amount of change B in absorbance (B=b'−b) during the reaction time span T2 is calculated based on the absorbances b and b'.

SS302 (Measuring Process)

The operation of the measuring unit in step SS302 is described below using FIG. 21. In step SS302, the absorbance is determined during a predetermined reaction time after the antigen-antibody reaction has been started by the addition of the carrier particle suspension. The light from the light source 50 is diffracted into a spectrum at 800 nm by the filter 51, and irradiates the container 49. The diffracted light passes through the assay sample in the container 49, and the transmitted light reaches the photodiode 52. The photodiode 52 receives the transmitted light, subjects the light to photoelectric conversion, and outputs the resulting electrical signal. Each output signal is transmitted to the controller. The output signals are sent to the controller and stored in the memory unit as data. Thus, the transmitted light from the assay sample is detected at predetermined reaction times in step SS302. The predetermined reaction times are the reaction times T1$a$, T1$a$', T2$b$, and T2$b$' set in step SS1.

SS303 (Analysis Process)

Figure 26:
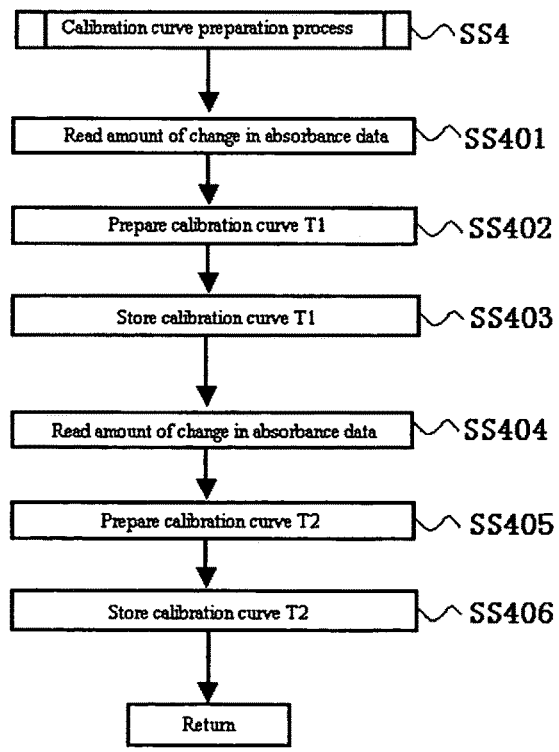
FIG. 26 illustrates the flow of the analysis process in the standard fluid measuring process in another embodiment of the present invention.

When the transmitted light is detected in step SS302, analysis is executed by the analyzing unit based on the analysis program. The operation of the analysis program in step SS303 is described below using the flow chart of FIG. 26. Each step of the flow chart is described below.

SS303-1: The data of the transmitted light signals are read from the memory unit. Then, the process advances to step SS303-2.

SS303-2: The absorbance is determined based on the transmitted light signal data. Then, the process continues to step S303-3.

SS303-3: The amount of change in absorbance in the reaction time span is calculated based on the absorbances calculated in step SS303-2. The amount of change A in absorbance at reaction time span T1 is calculated based on the absorbance a at reaction time T1$a$ and absorbance a' at reaction time T1$a$', and the amount of change B in absorbance at reaction time span T2 is calculated based on absorbance b at reaction time T2$b$ and absorbance b' at reaction time T2$b$'. Then, the process continues to step SS303-4.

SS303-4: the absorbance data calculated in step SS303-2 and the amount of change data calculated in step SS303-3 are stored in the memory unit.

The aforesaid is shown in the flow chart of step SS3 (standard solution measuring process). In this way the T1 standard solutions and T2 standard solutions are measured, and the amount of change in absorbance is calculated for each standard solution.

SS4 (Calibration Curve Preparation Process)

Figure 27:
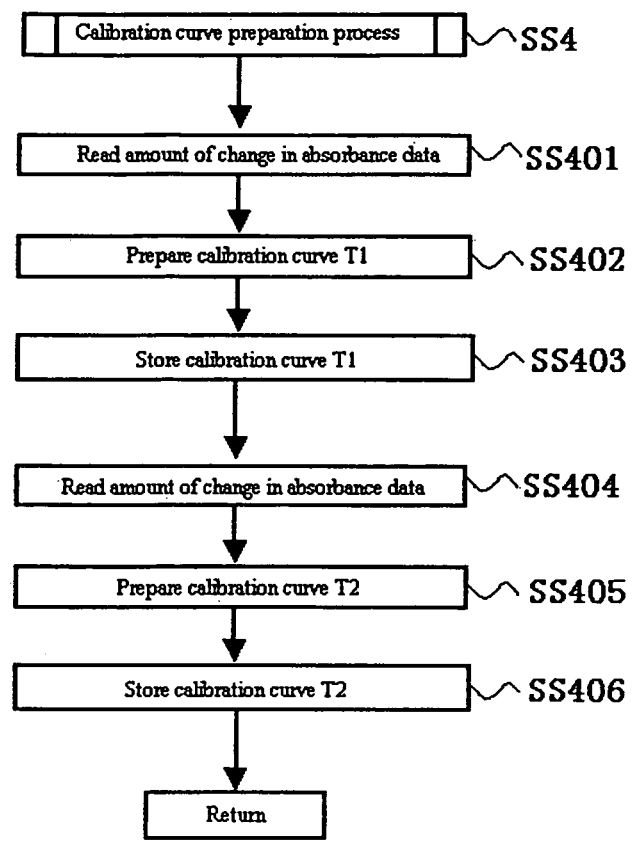
FIG. 27 illustrates the flow of the calibration curve preparing process in another embodiment of the present invention.

In step SS4, calibration curves are prepared based on the data of the amount of change in absorbance for each standard solution obtained in step SS3. The calibration curves prepared in step SS4 are calibration curve T1 prepared based on the data of the amount of change in absorbance during reaction time span T1, and calibration curve T2 based on the data of the amount of change in absorbance during the reaction time span T2. The calibration curve T1 is prepared based on the concentration of the assay material in the T1 standard solutions input in step SS1, and the amount of change in absorbance at reaction time T1 obtained by measuring the T1 standard solutions in step SS3. The calibration curve T2 is prepared based on the concentration of the assay material in the T2 standard solutions input in step SS1, and the amount of change in absorbance at reaction time T2 obtained by measuring the T2 standard solutions in step SS3. The operation of the analysis program in the calibration curve preparation process is described below using the flow chart of FIG. 27. Each step of the flow chart is described below.

SS401: The concentration of the assay material in each T1 standard solution, and the data on the amount of change in absorbance during reaction time span T1 calculated in step SS3 are read from the memory unit. Then, the process advances to step SS402.

SS402: The calibration curve T1 is prepared based on the concentrations and amount of change in absorbance. Then, the process advances to step SS403.

SS403: The calibration curve T1 prepared in step SS402 is stored in memory. Then, the process advances to step SS404.

SS404: The concentration of the assay material in each T2 standard solution, and the data on the amount of change in absorbance during reaction time span T2 calculated in step SS3 are read from the memory unit. Then, the process advances to step SS405.

SS405: The calibration curve T2 is prepared based on the concentrations and amount of change in absorbance. Then, the routine advances to step SS406.

SS406: The calibration curve T2 prepared in step SS405 is stored in memory.

The aforesaid is shown in the flow chart in step SS4 (calibration curve preparation process). Thus, the calibration curve T1 and calibration curve T2 are prepared in this manner.

SS5 ($\gamma$(T1) Setting Process)

In step SS5, a threshold value $\gamma$(T1) is set for the amount of change in absorbance during the reaction time span T1. In general, when calculating concentrations using a calibration curve, the concentration range capable of calculating a reliable value is a range in which the calibration curve is linear. For this reason, value have been determined based on the lower limit value of the range ensuring the linearity of the calibration curve T1 and the upper limit value of the range ensuring the linearity of the calibration curve T2, and have been stored as threshold value data in the memory unit of the apparatus beforehand. In the present step, the threshold value data are automatically read from the memory unit, and set as $\gamma$(T1). When $\gamma$(T1) is set in this way, the routine advances to step SS6 (specimen mode selection determination).

SS6 (Specimen Mode Selection Determination)

In step SS6, a determination is made as to whether or not the specimen mode has been selected based on the measurement conditions input in the mode setting process of step SS1. When [specimen mode] has been selected in step SS1, the process continues to step SS7 (specimen measuring process). When [specimen mode] is not selected in step SS1, however, the process advances to step SS9 (output process).

SS7 (Specimen Measuring Process)

Figure 28:
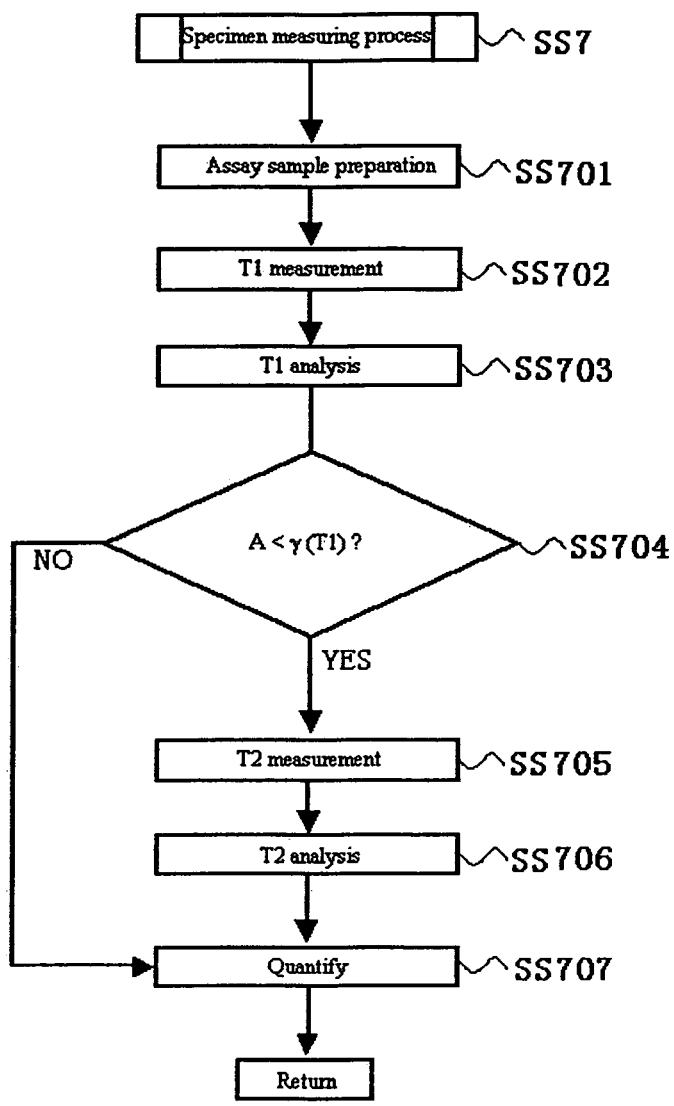
FIG. 28 illustrates the flow of the specimen measuring process in another embodiment of the present invention.

In step SS7, a specimen is measured, and the concentration of the assay material contained in the specimen is calculated based on the calibration curve prepared in step SS4, and the amount of change in the absorbance. FIG. 28 is a flow chart showing the flow of the specimen measuring process. In the specimen measuring process, step SS701 (assay sample preparation), step SS702 (T1 measurement), step SS703 (T1 analysis), step SS704 (determination whether to perform T2 measurement), step SS705 (T2 measurement), step SS706 (T2 analysis), and step SS707 (quantification) are sequentially performed under the conditions input in the mode setting process of step SS1.

SS701 (Assay Sample Preparation)

The operation of the assay sample preparation unit is described referring to FIG. 20. The dispensing device 46 first suctions specimen from the container placed in the specimen placement unit 42, and dispenses 15 µL of specimen into the container placed in the reaction unit 45. Then, the dispensing unit 46 suctions reaction buffer from the container placed in the reagent placement unit 44, and dispenses 10 µL to the container placed in the reaction unit 45. Then, the dispensing unit 46 suctions carrier suspension from the container 48 placed in the reagent placement unit 44, and dispenses 50 µL to the container placed in the reaction unit 45. The antigen-antibody reaction is started by the addition of the carrier particle suspension. The assay sample in the container in the reaction unit 45 is agitated while maintained at a temperature of 37° C.

SS702 (T1 Measurement)

In step SS702, the transmitted light signals at reaction times T1$a$ and T1$a$' input in step SS1 are detected. When assuming the reaction time T1$a$ is 10 seconds and reaction time T1$a$' is 60 seconds input in step SS1, the operation of the assay sample preparation unit and measuring unit are controlled by the control program such that the transmitted light is detected at reaction time T1$a$ 10 seconds after the start of the antigen-antibody reaction, and transmitted light is detected at reaction time T1$a$' 60 seconds after the start of the antigen-antibody reaction. The operation of the measuring unit in step SS702 is identical to the operation in step SS302 (measuring process), that is, the transmitted light signals are detected and the detected signals are stored in the memory unit.

SS703 (T1 Analysis)

When the transmitted light is detected in step SS702, T1 analysis is executed by the analyzing unit based on the analysis program. The operation of the analysis program in step SS703 is identical to the operation in step SS303 (analysis process), that is, the absorbance a detected at reaction time T1$a$ and the absorbance a' detected at reaction time T1$a$' are calculated. Then, the amount of change A in absorbance during reaction time span T1 is calculated based on absorbances a and a'. The data of the absorbances and the amount of change A in absorbance are stored in the memory unit.

SS704 (Determination of Whether to Perform T2 Measurement)

The amount of change A calculated in step SS703 is compared to the threshold value γ(T1) set in step SS5. When the amount of change A exceeds the threshold value γ(T1), measurements are not required at reaction times T2$b$ and T2$b'$ since the concentration of the assay material can be determined using the amount of change A during the reaction time span T1. In this case, therefore, the temperature maintenance and agitation in the container of the reaction unit 45 ends in the assay sample preparation unit, and the process advances to step SS707. When the amount of change A is less than the threshold value γ(T1), measurements are required at reaction times T2$b$ and T2$b'$ since the concentration of the assay material cannot be determined using the amount of change A during the reaction time span T1. At this time, therefore, the process advances to step SS705. Also at this time, the temperature maintenance and agitation in the reaction unit 45 is continued thereafter as before until reaction time T2$b'$.

SS705 (T2 Measurement)

SS705 is executed when the amount of change A is less than the threshold value γ(T1) in step SS704. In step SS705, the transmitted light signal is detected reaction time T2$b$ and reaction time T2$b'$ input in step SS1. When assuming the reaction time T2$b$ is 60 seconds and reaction time T2$b'$ is 180 seconds input in step SS1, the operation of the assay sample preparation unit and measuring unit are controlled by the control program such that the transmitted light is detected at reaction time T2$b$ 60 seconds after the start of the antigen-antibody reaction, and transmitted light is detected at reaction time T2$b'$ 180 seconds after the start of the antigen-antibody reaction. The operation of the measuring unit at the T2 measurements is identical to the operation in step SS302 (measuring process), that is, the transmitted light signals are detected and the detected signals are stored in the memory unit.

SS706 (T2 Analysis)

When the transmitted light signals are detected in step SS705, T2 analysis is executed by the analyzing unit based on the analysis program. The operation of the analysis program in step SS706 is identical to the operation in step SS303 (analysis process), that is, the absorbance b detected at reaction time T2$b$, and the absorbance b' detected at reaction time T2$b'$ are calculated. Then, the amount of change B in the absorbance during reaction time span T2 is calculated based on absorbances b and b'. The data of the absorbances and the amount of change B in absorbance are stored in the memory unit.

SS707 (Quantification)

In step SS707, the concentration of assay material contained in the specimen is calculated based on the amount of change in absorbance obtained in step SS703 or step SS706. When T2 measurement and T2 analysis are not performed, the concentration of the assay material contained in the specimen is calculated based on the amount of change A during the reaction time span T1, and the calibration curve T1. When the T2 measurement and T2 analysis are performed, however, the concentration of the assay material contained in the specimen is calculated based on the amount of change B during the reaction time T2, and the calibration curve T2. Then, the concentration data calculated in step SS707 are stored in the memory unit.

SS708 (All Specimens Completed)

When a plurality of specimens are assayed, step SS8 is repeated until [measurement of all specimens has been completed] has been determined in step SS8. When the measurement of all specimens has been completed, the process advances to step SS9.

SS9 (Output Process)

The data of the amount of change in absorbance of the standard solutions stored in step SS3, and the data of the concentration and amount of change in absorbance of specimens stored in step SS7 are output and displayed on the liquid crystal touch panel.

The aforesaid steps are shown in the flow chart of the general control in the present embodiment. As described above, the biological sample analyzing apparatus 41 is an automatic analyzer that performs automatically from the preparation of the assay sample to the quantification of the assay material.

(Measurement Example 5)

The measurement results shown were taken when the reaction time T1$a$ was set at 10 sec, T1$a'$ was set at 60 seconds, and reaction time T2$b$ was set at 60 sec, and T2$b'$ was set at 180 seconds using the previously described biological sample analyzing apparatus 41. In the present example, the threshold γ(T1) was set at 0.01 for the amount of change in absorbance. In this way if the amount of change A exceeds 0.01, the CRP concentration contained in the specimen is calculated based on the amount of change A at reaction time T1 and the calibration curve T1. In this way if the amount of change A is less than 0.01, the CRP concentration contained in the specimen is calculated based on the amount of change B at reaction time T2.

COBAS reagent CRPLX (manufactured by Roche Diagnostics) was used in the measurement of this example. This reagent is provided in a reagent kit, which includes latex reagent containing latex particle on which anti-human CRP mouse monoclonal antibody is immobilized and TRIS buffer solution. The buffer solution was used as the reaction buffer, and the latex reagent was sued as the carrier particle suspension.

The standard solution was LZ test for CRP standard serum Eiken' manufactured by Eiken Chemical Co., Ltd. The standard solutions contained CRP concentrations of 0, 0.5, 4, 12, 22, and 30 mg/dL. CRP concentrations of 0, 0.5, 4, and 12 mg/dL were used in T1 standard solutions, and CRP concentrations of 0, 0.5, 4, 12, 22, and 30 mg/dL were used in T2 standard solutions.

In the present example, plasmas 1~16 containing various concentrations of CRP were used as specimens.

These same specimens were measured to determine concentration of CRP contained in the specimens using a model TBA-80FR NEO2 Clinical Autochemical Analyzer manufactured by Toshiba Corporation. CRP latex (II) 'Seiken' X2 manufactured by Denka Seiken Co., Ltd. was used as the reagent. (Hereinafter measurements using the TBA-80FR NEO2 are referred to as 'comparative measurements'.) In the comparative measurements, absorbance was measured at a reaction times of 50 seconds and 158 seconds, and the amount of change in absorbance was calculated during the time 50 seconds after to the start of the reaction to 158 seconds after the start of the reaction based on these absorbances.

Table 3 shows the results obtained by measuring each specimen using the biological sample analyzing apparatus 41. In Table 3, column [A] shows the values of amount of change A during reaction time span T1, and column [B] shows the values of amount of change B during reaction time span T2. [Calibration curve] indicates the calibration curve used when calculating concentration, T1 indicating Calibration curve T1 was used, and T2 indicating calibration curve T2 was used. [Concentration I] indicates the CRP concentration (mg/dL) obtained by measurements using the biological sample analyzing apparatus 41, and [concentration II] indicating CRP concentration (mg/dL) obtained by measurements of the comparative examples.

TABLE 3

| Specimen | A | B | Calibration curve | Concentration I (mg/dL) | Concentration II (mg/dL) |
|---|---|---|---|---|---|
| Plasma 1 | 0.0014 | 0.0003 | T2 | 0.01 | 0.02 |
| Plasma 2 | 0.0022 | 0.0005 | T2 | 0.02 | 0.03 |
| Plasma 3 | 0.0030 | 0.0016 | T2 | 0.06 | 0.05 |
| Plasma 4 | 0.0032 | 0.0031 | T2 | 0.14 | 0.11 |
| Plasma 5 | 0.0045 | 0.0046 | T2 | 0.20 | 0.17 |
| Plasma 6 | 0.0065 | 0.0055 | T2 | 0.22 | 0.18 |
| Plasma 7 | 0.0062 | 0.0065 | T2 | 0.26 | 0.23 |
| Plasma 8 | 0.0123 | — | T1 | 0.58 | 0.52 |
| Plasma 9 | 0.0358 | — | T1 | 2.06 | 1.75 |
| Plasma 10 | 0.0826 | — | T1 | 4.85 | 4.22 |
| Plasma 11 | 0.1139 | — | T1 | 6.64 | 5.64 |
| Plasma 12 | 0.1463 | — | T1 | 8.48 | 7.25 |
| Plasma 13 | 0.2337 | — | T1 | 13.3 | 11.0 |
| Plasma 14 | 0.2873 | — | T1 | 16.8 | 14.7 |
| Plasma 15 | 0.3883 | — | T1 | 21.2 | 18.0 |
| Plasma 16 | 0.4637 | — | T1 | 29.6 | 25.9 |

According to Table 3, the CRP concentrations calculated using the measurements of the biological sample analyzing apparatus 41 approximate the concentrations determined by the comparative measurements. In the biological sample analyzing apparatus 41, the CRP concentration calculation for specimens with relatively high CRP concentrations (sera 8~16) is based on the amount of change A during reaction time span T1. It can also be understood from Table 3 with regards to specimens having relatively high CRP concentrations (sera 8~16), that the CRP concentrations calculated using the measurements of the biological sample analyzing apparatus 41 approximate the concentrations determined using the comparative measurements. Accordingly, when measuring specimens with high concentrations, the biological sample analyzing apparatus 41 can calculate concentrations faster than calculations by the comparative measurements.

(Measurement Example 6)

The measurement results indicated here are from whole blood measurements using the biological sample analyzing apparatus 41 described above.

When whole blood was used directly as a specimen, there was concern that the measurement would be affected by the hemocyte component (mainly red blood cells) contained in the whole blood, such that an accurate measurement result could not be obtained. In the present example, a hemolytic agent, STROMATOLYSER-WH, manufactured by Sysmex Corporation, was diluted three fold using a dilution fluid also manufactured by Sysmex corporation, and this was mixed with whole blood in a hemolytic process to obtain a specimen used for measurement.

When whole blood is used as a specimen in the same quantity as when plasma and serum is used for measurement, the hemocyte component (hemocyte volume) is reflected in the low measurement values. Therefore, the hemocyte volume must be compensated when measurements are performed using whole blood. In the present example, this compensation is accomplished by the following method. Specifically, whole blood specimens were measured using a model XE-2100 fully automatic hemocyte analyzer manufactured by Sysmex corporation to determine the hemocyte count, and the hematocrit value was determined based on this hemocyte count. (The hematocrit value represents the percentage volume of red blood cells in a constant volume of whole blood.) The equation below was then used for the compensation.

$$C = C0 / \{1 - (H/100)\}$$

(Where C represents the compensated concentration of the assay material, Co represents the concentration of the assay material obtained by measuring whole blood, and H represents the hematocrit value (%).)

The reaction time in the measurements of the present example were $T1a=10$ seconds, $T1a'=60$ seconds, $T2b=60$ seconds, and $T2b'=180$ seconds. Each type of reagent and standard solution used in the present example were identical to the reagents and standard solutions used in measurement example 5. Furthermore, in the present example, whole blood 1~11 containing various concentrations of CRP were prepared, and 100 μL of three-fold diluted STROMATOLYSER-WH was added to 20 μL whole blood to obtain usable specimens. For comparison purposes in the present example, plasma 1~11 were prepared by centrifuging (8,000 rpm for 5 minutes) the whole blood 1~11, and 100 μL three-fold diluted STROMATOLYSER-WH was added to 20 μL of the plasma to obtain usable specimens.

Table 4 shows the results obtained by measuring each specimen using the biological sample analyzing apparatus 41. [Calibration curve] indicates the calibration curve used when calculating concentration, T1 indicating calibration curve T1 was used, and T2 indicating calibration curve T2 was used. [Concentration] indicates the CRP concentration (mg/dL) obtained by measurements using the biological sample analyzing apparatus 41.

TABLE 4

| Specimen | Calibration curve | Concentration (mg/dL) |
|---|---|---|
| Whole blood 1 | T2 | 0.01 |
| Whole blood 2 | T2 | 0.07 |
| Whole blood 3 | T2 | 0.14 |
| Whole blood 4 | T2 | 0.19 |
| Whole blood 5 | T2 | 0.28 |
| Whole blood 6 | T1 | 2.35 |
| Whole blood 7 | T1 | 4.11 |
| Whole blood 8 | T1 | 9.19 |
| Whole blood 9 | T1 | 15.27 |
| Whole blood 10 | T1 | 19.31 |
| Whole blood 11 | T1 | 26.39 |
| Plasma 1 | T2 | 0.02 |
| Plasma 2 | T2 | 0.09 |
| Plasma 3 | T2 | 0.14 |
| Plasma 4 | T2 | 0.20 |
| Plasma 5 | T2 | 0.26 |
| Plasma 6 | T1 | 2.06 |
| Plasma 7 | T1 | 4.09 |
| Plasma 8 | T1 | 9.89 |
| Plasma 9 | T1 | 16.80 |
| Plasma 10 | T1 | 19.79 |
| Plasma 11 | T1 | 28.07 |

When the CRP concentrations of the whole blood specimens and plasma specimens of the same reference numbers (Whole blood 1 and plasma 1, whole blood 2 and plasma 2, whole blood 3 and plasma 3) in Table 4 were compared, it was observed that the whole blood CRP concentrations approximated the plasma CRP concentrations in all cases. This indicated that whole blood could also be measured.

In the present embodiment, measurements were performed during different reaction time bands (reaction time span T1 and reaction time span T2). When the reaction time $T1a$, $T1a'$, $T2b$, and $T2b'$ are set such that $T1a<T1a'$ and $T2b<T2b'$, and $T1a<T2b$ and $T1a'<T2b'$, the reaction during the reaction time span T2 is generally comparatively stable compared to the reaction during reaction time span T1. Therefore, the measurements during the reaction time span T2, which has a relatively stable reaction, have between reproducibility and sensitivity than measurements during the reaction time span T1, which has a relatively unstable reaction. For this reason, the calibration curve T2 during the reaction time span T2 is particularly useful when calculating the concentration of assay material of low concentration. Measurement during the reaction time span T1, however, are less easily affected by the zone phenomenon than measurements during the reaction time span T2. For this reason, the calibration curve T1 during the reaction time span T1 is particularly useful when calculating the concentration of assay material of high concentration.

In the present embodiment, predetermined conditions are provided related to measurement results during the reaction time span T1, such that the calibration curve T1 is used when calculating the concentration of assay material that has high concentration, and the calibration curve T2 is used when calculating the concentration of assay material that has low concentration. For this reason, measurements at both a first reaction time span (reaction time span T1) and a second reaction time span (reaction time span T2) are not always necessary, and measurements during the reaction time span T2 are performed only when the measurement result during the reaction time span T1 do not satisfy the predetermined conditions. In this way measurements can be accomplished more efficiently on a time basis.

In the present embodiment, the reaction time span T1 and reaction time span T2 can be set by the operator in accordance with the measurement range required. In this way measurement can be accomplished more efficiently without measuring over a time period longer than necessary.

Although reaction time T1$a$=10 seconds, T1$a'$=60 seconds, T2$b$=60 seconds, and T2$b'$=180 seconds in the above embodiments, the reaction times are not limited to these settings. The times of suitable reaction times T1$a$, T1$a'$, T2$b$, T2$b'$ may differ depending on the assay material. For this reason, suitable reaction times T1$a$, T1$a'$, T2$b$, T2$b'$ may be set in accordance with the assay material to be measured.

Although the transmitted light is detected by illuminating an assay sample with light having a wavelength of 800 nm in the above embodiments, light of an optimum wavelength may be selected and used for measurement in accordance with the measurement conditions and reagents.

Although serum, plasma, and whole blood collected from humans are used as specimen in the two embodiments, the present invention is not limited to these. In the present invention, other biological sample, such as urine and the like, may be used as specimen.

Latex on which anti-CRP antibody is immobilized is used as the carrier particle in the above two embodiments, the present invention is not limited to this arrangement. Other carrier particles may be used insofar as such carrier particles on which antibody or antigen against the assay material is immobilized. The antibody or antigen immobilized on carrier particles are not specifically limited insofar as they are detectable using an antigen-antibody reaction. The method for immobilization of antigen or antibody on carrier particle may be well known methods in the art. For example, physical absorption methods, chemical bonding methods and the like may be used.

Although CRP is detected as the assay material in the above two embodiments, the present invention is not limited to this arrangement. Other materials may be detected as assay materials insofar as such assay materials are detectable in immunoassays using carrier particles. Examples of assay materials include immunoglobulin (IgG, IgA, IgM, IgD, IgE) complements (C3, C4, C5, C1$q$), α-fetoprotein (AFP), β2-microglobulin, carcinoembryonic antigen (CEA), prostate specific antigen (PSA), anti HCV antibody, insulin, ferritin and the like.

Although the amount of change in absorbance obtained by immunoturbidity and the agglutination rate in CIA are used as information related to the assay material in the above two embodiments, it is to be noted that the information related to the assay material is not limited to such information. For example, since transmitted light, absorbance, scattered light obtained by illuminating an assay sample with light, or the amount of change in these parameters per predetermined unit time varies depending on the degree of agglutination in the assay sample, information related to the assay material in the assay sample may be used.

Although the immunoturbidity method employing carrier particles and CIA is used as the method for quantifying assay material in the above two embodiments, the present invention is not limited to these methods. For example, immunonephelometry employing carrier particles also may be used. Furthermore, immunoturbidity methods that do not use carrier particles and immunonephelometry methods that do not use carrier particles also may be used.

Although data of the threshold values α(T1) and γ(T1) stored beforehand in the memory unit of the apparatus, and data stored when setting the threshold values are automatically read and set as the threshold values in the above two embodiments, the present invention is not limited to this arrangement. For example, a program capable of automatically setting threshold values based on calibration curve data may be installed in the apparatus, the program may be automatically started when setting a threshold, the threshold value may then be automatically calculated based on the data such as a calibration curve, and the calculated value can be set as a threshold value.

The invention claimed is:

1. A biological sample analyzing apparatus comprising:
an assay sample preparation unit comprising a mixing container and a dispenser operable to aspirate a testing reagent, which contains carrier particles with a substance for causing an antigen-antibody reaction, and a biological sample, which is selected from a group consisting of blood, urine, whole blood, plasma and serum and contains an assay material reactive with the substance through the antigen-antibody reaction, in the mixing container to prepare an assay sample in which some of the carrier particles are agglutinated by the assay material reacted with the substance and a reminder of the carrier particles are not agglutinated;
a measuring unit comprising a flow cell through which the assay sample including the agglutinated carrier particles and the unagglutinated particles is flown, and a laser light source operable to irradiate a laser light to the agglutinated and unagglutinated carrier particles in the assay sample flowing through the flow cell, the measuring unit further comprising a light detector configured to detect a light scattered from the agglutinated and unagglutinated carrier particles in the assay sample flowing through the flow cell, wherein the scattered light carries size information indicative of a size of a respective one of the agglutinated and unagglutinated carrier particles in the assay sample, and the agglutinated and unagglutinated carrier particles in the assay sample are distinguishable from each other by the size information;

a display device; and a controller computer programmed to perform operations comprising:

operating a memory to store first and second calibration curves, wherein the first calibration curve represents a relationship between an agglutination rate and a concentration of the assay material in the assay sample which has undergone the antigen-antibody reaction for a first reaction time, and the second calibration curve represents a relationship between the agglutination rate and the concentration of the assay material in the assay sample which has undergone the antigen-antibody reaction for a second reaction time which is longer than the first reaction time;

operating the memory to store a predetermined threshold value representative of a a lower limit of a range of the first calibration curve;

operating the assay sample preparation unit to mix the testing reagent and the biological sample in the mixing container to prepare a first quantity of the assay sample, wherein the first quantity of the assay sample undergoes the antigen-antibody reaction for the first reaction time;

operating the measuring unit to flow the first quantity of the assay sample through the flow cell and irradiate the laser thereto to detect first size information indicative of a size of a respective one of the agglutinated and unagglutinated carrier particles in the first quantity of the assay sample;

analyze the first size information to determine a number of the agglutinated particles and a number of the unagglutinated particles in the first quantity of the assay sample;

determining a first agglutination rate of the assay material in the first quantity of the assay sample, wherein the first agglutination rate is a ratio (P/T) between the number of the agglutinated particles determined from the first size information and a total number of the agglutinated and unagglutinated particles determined from the first size information;

comparing the first agglutination rate with the predetermined threshold value stored in the memory;

responsive to a determination that the first agglutination rate exceeds the predetermined threshold, reading, from the first calibration curve stored in the memory, a concentration of the assay material in the first quantity of the assay sample corresponding to the first agglutination rate; and displaying on the display device the concentration of the assay material, and in response to a determination that the first agglutination rate does not exceed the predetermined threshold, the controller computer further programmed to perform operations comprising:

operating, the measuring unit to flow a second quantity of the assay sample through the flow cell, wherein the second quantity of the assay sample undergoes the antigen-antibody reaction for the second reaction time, and irradiate the laser thereto to detect second size information indicative of a size of a respective one of the agglutinated and unagglutinated carrier particles in the second quantity of the assay sample;

analyzing the second size information to determine a number of the agglutinated particles and a number of the unagglutinated particles in the second quantity of the assay sample;

determining a second agglutination rate of the assay material in the second quantity of the assay sample, wherein the second agglutination rate is a ratio (P/T) between the number of agglutinated particles determined from the second size information and a total number of the agglutinated and unagglutinated particles determined from the second size information;

reading, from the second calibration curve stored in the memory, a concentration of the assay material in the second quantity of the assay sample corresponding to the second agglutination rate; and displaying on the display device the concentration of the assay material.

2. The biological sample analyzing apparatus according to claim 1, wherein the operations further comprise preparing the first calibration curve and the second calibration curve, wherein the operations of preparing the first and second calibration curves comprises:

operating the assay sample preparation unit to mix the testing reagent with a plurality of standard solutions of different concentrations to prepare a plurality of assay samples of different concentrations;

operating the measuring unit to flow a third quantity of a respective assay sample through the flow cell and irradiate the laser thereto to detect third size information indicative of a size of a respective one of the agglutinated and unagglutinated carrier particles in the third quantity of the respective assay sample, wherein the third quantity of the respective assay sample undergoes the antigen-antibody reaction for the first reaction time;

operating the measuring unit to flow a fourth quantity of a respective assay sample through the flow cell and irradiate the laser thereto to detect fourth size information indicative of a size of a respective one of the agglutinated and unagglutinated carrier particles in the fourth quantity of the respective assay sample, wherein the fourth quantity of the respective assay sample undergoes the antigen-antibody reaction for the second reaction time;

analyze the third size information to determine a number of the agglutinated particles and a number of the unagglutinated particles in the third quantity of the respective assay sample;

determining a third agglutination rate of the assay material in the third quantity of the respective assay sample, wherein the third agglutination rate is a ratio between the number of the agglutinated particles determined from the third size information and a total number of the agglutinated and unagglutinated particles determined from the third size information:

analyze the fourth size information to determine a number of the agglutinated particles and a number of the unagglutinated particles in the fourth quantity of the respective assay sample;

determining a fourth agglutination rate of the assay material in the fourth quantity of the respective assay sample, wherein the fourth agglutination rate is a ratio between the number of the agglutinated particles determined from the fourth size information and a total number of the agglutinated and unagglutinated particles determined from the fourth size information;

plotting the third agglutination rates in relation to the concentrations of the assay samples to derive the first calibration curve, and plotting the fourth agglutination rates in relation to the concentrations of the standard solutions to derive the second calibration curve.

3. The biological sample analyzing apparatus according to claim 1, herein the testing reagent comprises antibody or antigen that binds to the assay material.

4. The biological sample analyzing apparatus according to claim 3, wherein the antibody or antigen is immobilized on the carrier particles.

5. A biological sample analyzing method comprising the steps of:
- storing first and second calibration curves, wherein the first calibration curve represents a relationship between an agglutination rate and a concentration of an assay material in an assay sample which has undergone the antigen-antibody reaction for a first reaction time, and the second calibration curve represents a relationship between the agglutination rate and the concentration of the assay material in the assay sample which has undergone the antigen-antibody reaction for a second reaction time which is longer than the first reaction time;
- storing a predetermined threshold value representative of a lower limit of a range of the first calibration curve;
- mixing a testing reagent, which contains carrier particles with a substance for causing an antigen-antibody reaction, and a biological sample, which is selected from a group consisting of blood, urine, whole blood, plasma and serum and contains the assay material reactive with the substance through the antigen-antibody reaction, to prepare the assay sample in which some of the carrier particles are agglutinated by the assay material reacted with the substance and a reminder of the carrier particles are not agglutinated;
- flowing a first quantity of the assay sample through a flow cell and irradiating a laser to the agglutinated and unagglutinated carrier particles in the first quantity of the assay sample flowing through the flow cell, wherein the first quantity of the assay sample undergoes the antigen-antibody reaction for the first reaction time;
- detecting a light scattered from the agglutinated and unagglutinated carrier particles in the first quantity of the assay sample flowing through the flow cell, wherein the scattered light carries first size information indicative of a size of a respective one of the agglutinated and unagglutinated carrier particles in the first quantity of the assay sample, and the agglutinated and unagglutinated carrier particles in the first quantity of the assay sample are distinguishable from each other by the first size information;
- analyzing the first size information to determine a number of the agglutinated particles and a number of the unagglutinated particles in the first quantity of the assay sample;
- determining a first agglutination rate of the assay material in the first quantity of the assay sample, wherein the first agglutination rate is a ratio (P/T) between the number of the agglutinated particles determined from the first size information and a total number of the agglutinated and unagglutinated particles determined from the first size information;
- comparing the first agglutination rate with the predetermined threshold value;
- in response to a determination that the first agglutination rate exceeds the predetermined threshold value, reading from the first calibration curve a concentration of the assay material in the first quantity of the assay sample corresponding to the first agglutination rate; and
- displaying on a display device the concentration of the assay material, and
- in response to a determination that the first agglutination rate does not exceed the predetermined threshold, flowing a second quantity of the assay sample through a flow cell and irradiating a laser to the agglutinated and unagglutinated carrier particles in the second quantity of the assay sample flowing through the flow cell, wherein the second quantity of the assay sample undergoes the antigen-antibody reaction for the second reaction time;
- detecting a light scattered from the agglutinated and unagglutinated carrier particles in the second quantity of the assay sample flowing through the flow cell, wherein the scattered light carries second size information indicative of a size of a respective one of the agglutinated and unagglutinated carrier particles in the second quantity of the assay sample, and the agglutinated and unagglutinated carrier particles in the second quantity of the assay sample are distinguishable from each other by the second size information;
- analyzing the second size information to determine a number of the agglutinated particles and a number of the unagglutinated particles in the second quantity of the assay sample;
- determining a second agglutination rate of the assay material in the second quantity of the assay sample, wherein the second agglutination rate is a ratio (P/T) between the number of the agglutinated particles determined from the second size information and a total number of the agglutinated and unagglutinated particles determined from the second size information;
- reading from the second calibration curve a concentration of the assay material in the second quantity of the assay sample corresponding to the second agglutination rate; and
- displaying on the display device the concentration of the assay material.

6. The biological sample analyzing method according to claim 5, wherein the testing reagent contains antibody or antigen that binds to the assay material.

7. The biological sample analyzing method according to claim 5, wherein the antibody or antigen is immobilized on the carrier particles.

8. The biological sample analyzing apparatus according to claim 1, wherein the scattered light is forward scattered light.

9. The biological sample analyzing apparatus according to claim 5, wherein the scattered light is forwarded scattered light.

10. The biological sample analyzing apparatus according to claim 1, wherein a difference between the first and second reaction times is selected based on a type of material comprised by the assay sample.

* * * * *

UNITED STATES PATENT AND TRADEMARK OFFICE
CERTIFICATE OF CORRECTION

PATENT NO. : 9,568,488 B2
APPLICATION NO. : 11/255576
DATED : February 14, 2017
INVENTOR(S) : Teruya Matsumoto et al.

Page 1 of 1

It is certified that error appears in the above-identified patent and that said Letters Patent is hereby corrected as shown below:

In the Claims

In Column 33, Claim 1, Line 17, after "representative of" replace "aa lower" with --a lower--.

Signed and Sealed this
Twenty-fourth Day of April, 2018

Andrei Iancu
*Director of the United States Patent and Trademark Office*